(12) United States Patent
Bardy

(10) Patent No.: US 8,731,648 B2
(45) Date of Patent: May 20, 2014

(54) SYSTEM AND METHOD FOR PRIORITIZING MEDICAL CONDITIONS

(71) Applicant: Cardiac Pacemakers, Inc., St. Paul, MN (US)

(72) Inventor: Gust Bardy, Carnation, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/758,262

(22) Filed: Feb. 4, 2013

(65) Prior Publication Data

US 2013/0158361 A1  Jun. 20, 2013

Related U.S. Application Data

(60) Division of application No. 13/312,174, filed on Dec. 6, 2011, now Pat. No. 8,369,937, which is a continuation of application No. 11/512,689, filed on Aug. 29, 2006, now Pat. No. 8,092,382, which is a division of application No. 10/976,665, filed on Oct. 29, 2004, now Pat. No. 7,117,028, which is a continuation of application No. 10/646,112, filed on Aug. 22, 2003, now Pat. No. 6,951,539, which is a continuation of application No. 10/210,418, filed on Jul. 31, 2002, now Pat. No. 6,834,203, which is a continuation of application No. 09/441,405, filed on Nov. 16, 1999, now Pat. No. 6,440,066.

(51) Int. Cl.
*A61B 5/04* (2006.01)

(52) U.S. Cl.
USPC .................................................. 600/513

(58) Field of Classification Search
USPC .......... 128/923–925; 600/301, 513, 515–518, 600/483
See application file for complete search history.

(56) References Cited

U.S. PATENT DOCUMENTS

| 3,837,339 A | 9/1974 | Aisenberg et al. |
| 4,142,533 A | 3/1979 | Brownlee et al. |
| 4,197,856 A | 4/1980 | Northrop |
| 4,531,527 A | 7/1985 | Reinhold, Jr. et al. |
| 4,686,999 A | 8/1987 | Snyder et al. |

(Continued)

FOREIGN PATENT DOCUMENTS

| EP | 0342859 | 11/1989 |
| EP | 0513457 | 11/1992 |

(Continued)

OTHER PUBLICATIONS

"File History", for EP Patent Application No. 00650198.5 corresponding to U.S. Appl. No. 09/441,405 (133 pages).

(Continued)

*Primary Examiner* — George Evanisko
(74) *Attorney, Agent, or Firm* — Pauly, DeVries Smith & Deffner LLC

(57) ABSTRACT

The technology disclosed herein generally relates to a method for providing an index disorder in automated patient care. A set of device measures is stored in a database. Quantitative health care data indicators in the database are provided, where the indicators were regularly recorded by a medical device for a patient under automated patient care. Collected device measures are retrieved with a processor. An index disorder is identified through derived measure determination and statistical calculation with a processor.

7 Claims, 18 Drawing Sheets

(56) References Cited

U.S. PATENT DOCUMENTS

| | | |
|---|---|---|
| 4,803,625 A | 2/1989 | Fu et al. |
| 4,809,697 A | 3/1989 | Causey, III et al. |
| 4,852,570 A | 8/1989 | Levine |
| 4,899,758 A | 2/1990 | Finkelstein et al. |
| 4,958,645 A | 9/1990 | Cadell et al. |
| 4,974,607 A | 12/1990 | Miwa |
| 4,987,897 A | 1/1991 | Funke |
| 5,040,536 A | 8/1991 | Riff |
| 5,113,859 A | 5/1992 | Funke |
| 5,113,869 A | 5/1992 | Nappholz et al. |
| 5,133,346 A | 7/1992 | Kulkarni |
| 5,199,428 A | 4/1993 | Obel et al. |
| 5,301,105 A | 4/1994 | Cummings, Jr. |
| 5,309,919 A | 5/1994 | Snell et al. |
| 5,313,593 A | 5/1994 | Barakat et al. |
| 5,331,549 A | 7/1994 | Crawford, Jr. |
| 5,336,245 A | 8/1994 | Adams et al. |
| 5,355,889 A | 10/1994 | Nevo et al. |
| 5,357,427 A | 10/1994 | Langen et al. |
| 5,390,238 A | 2/1995 | Kirk et al. |
| 5,416,695 A | 5/1995 | Stutman et al. |
| 5,421,343 A | 6/1995 | Feng |
| 5,437,278 A | 8/1995 | Wilk |
| 5,438,983 A | 8/1995 | Falcone |
| 5,464,012 A | 11/1995 | Falcone |
| 5,544,661 A | 8/1996 | Davis et al. |
| 5,553,609 A | 9/1996 | Chen et al. |
| 5,557,514 A | 9/1996 | Seare et al. |
| 5,576,952 A | 11/1996 | Stutman et al. |
| 5,584,868 A | 12/1996 | Salo et al. |
| 5,591,215 A | 1/1997 | Greenhut et al. |
| 5,603,331 A | 2/1997 | Heemels et al. |
| 5,660,183 A | 8/1997 | Chiang et al. |
| 5,673,691 A | 10/1997 | Abrams et al. |
| 5,687,734 A | 11/1997 | Dempsey et al. |
| 5,697,959 A | 12/1997 | Poore |
| 5,704,345 A | 1/1998 | Berthon-Jones et al. |
| 5,704,366 A | 1/1998 | Taklind et al. |
| 5,711,297 A | 1/1998 | Iliff |
| 5,713,350 A | 2/1998 | Yokota et al. |
| 5,720,770 A | 2/1998 | Nappholz et al. |
| 5,720,771 A | 2/1998 | Snell |
| 5,724,580 A | 3/1998 | Levin et al. |
| 5,724,983 A | 3/1998 | Seiker et al. |
| 5,738,102 A | 4/1998 | Lemelson |
| 5,743,267 A | 4/1998 | Nikolic et al. |
| 5,749,907 A | 5/1998 | Mann |
| 5,749,908 A | 5/1998 | Snell |
| 5,752,976 A | 5/1998 | Duffin et al. |
| 5,769,074 A | 6/1998 | Barnhill et al. |
| 5,772,586 A | 6/1998 | Heinonen et al. |
| 5,772,599 A | 6/1998 | Nevo et al. |
| 5,772,604 A | 6/1998 | Langberg et al. |
| 5,778,882 A | 7/1998 | Raymond et al. |
| 5,785,650 A | 7/1998 | Akasaka et al. |
| 5,785,660 A | 7/1998 | Van Lake et al. |
| 5,788,640 A | 8/1998 | Peters |
| 5,792,062 A | 8/1998 | Poon et al. |
| 5,819,251 A | 10/1998 | Kremer et al. |
| 5,855,593 A | 1/1999 | Olson et al. |
| 5,860,918 A | 1/1999 | Schradi et al. |
| 5,876,353 A | 3/1999 | Riff |
| 5,879,375 A | 3/1999 | Larson, Jr. et al. |
| 5,891,178 A | 4/1999 | Mann et al. |
| 5,897,493 A | 4/1999 | Brown |
| 5,911,132 A | 6/1999 | Sloane |
| 5,931,857 A | 8/1999 | Prieve et al. |
| 5,954,640 A | 9/1999 | Szabo |
| 5,957,861 A | 9/1999 | Combs et al. |
| 5,974,124 A | 10/1999 | Schlueter, Jr. et al. |
| 5,987,352 A | 11/1999 | Klein et al. |
| 5,993,386 A | 11/1999 | Ericsson |
| 6,004,276 A | 12/1999 | Wright et al. |
| 6,014,581 A | 1/2000 | Whayne et al. |
| 6,024,699 A | 2/2000 | Surwit et al. |
| 6,038,469 A | 3/2000 | Karlsson et al. |
| 6,047,203 A | 4/2000 | Sackner et al. |
| 6,050,940 A | 4/2000 | Braun et al. |
| 6,063,028 A | 5/2000 | Luciano |
| 6,067,466 A | 5/2000 | Selker et al. |
| 6,073,046 A | 6/2000 | Patel et al. |
| 6,080,106 A | 6/2000 | Lloyd et al. |
| 6,083,248 A | 7/2000 | Thompson |
| 6,093,146 A | 7/2000 | Filangeri |
| 6,095,985 A | 8/2000 | Raymond et al. |
| 6,102,856 A | 8/2000 | Groff et al. |
| 6,122,351 A | 9/2000 | Schlueter, Jr. et al. |
| 6,129,675 A | 10/2000 | Jay |
| 6,135,951 A | 10/2000 | Richardson et al. |
| 6,139,494 A | 10/2000 | Cairnes |
| 6,152,882 A | 11/2000 | Prutchi |
| 6,155,267 A | 12/2000 | Nelson |
| 6,168,563 B1 | 1/2001 | Brown |
| 6,168,653 B1 | 1/2001 | Myers |
| 6,171,237 B1 | 1/2001 | Avitall et al. |
| 6,171,256 B1 | 1/2001 | Joo et al. |
| 6,203,495 B1 | 3/2001 | Bardy |
| 6,221,011 B1 | 4/2001 | Bardy |
| 6,223,078 B1 | 4/2001 | Marcovecchio |
| 6,225,901 B1 | 5/2001 | Kail, IV |
| 6,234,964 B1 | 5/2001 | Iliff |
| 6,246,992 B1 | 6/2001 | Brown |
| 6,249,705 B1 | 6/2001 | Snell |
| 6,250,309 B1 | 6/2001 | Krichen et al. |
| 6,263,245 B1 | 7/2001 | Snell |
| 6,283,923 B1 | 9/2001 | Finkelstein et al. |
| 6,287,252 B1 | 9/2001 | Lugo |
| 6,290,646 B1 | 9/2001 | Cosentino et al. |
| 6,302,844 B1 | 10/2001 | Walker et al. |
| 6,306,088 B1 | 10/2001 | Krausman et al. |
| 6,312,378 B1 | 11/2001 | Bardy |
| 6,336,900 B1 | 1/2002 | Alleckson et al. |
| 6,336,903 B1 | 1/2002 | Bardy |
| 6,363,282 B1 | 3/2002 | Nichols et al. |
| 6,368,284 B1 | 4/2002 | Bardy |
| 6,398,728 B1 | 6/2002 | Bardy |
| 6,411,840 B1 | 6/2002 | Bardy |
| 6,416,471 B1 | 7/2002 | Kumar et al. |
| 6,428,483 B1 | 8/2002 | Carlebach |
| 6,440,066 B1 * | 8/2002 | Bardy ............ 600/300 |
| 6,442,433 B1 | 8/2002 | Linberg |
| 6,454,705 B1 | 9/2002 | Cosentino et al. |
| 6,477,424 B1 | 11/2002 | Thompson et al. |
| 6,662,032 B1 | 12/2003 | Gavish et al. |
| 6,827,670 B1 | 12/2004 | Stark et al. |
| 6,834,203 B2 * | 12/2004 | Bardy ............ 600/518 |
| 6,951,539 B2 * | 10/2005 | Bardy ............ 600/301 |
| 7,117,028 B2 * | 10/2006 | Bardy ............ 600/513 |
| 8,092,382 B2 * | 1/2012 | Bardy ............ 600/301 |
| 8,369,937 B2 * | 2/2013 | Bardy ............ 600/513 |

FOREIGN PATENT DOCUMENTS

| | | |
|---|---|---|
| EP | 0531889 | 3/1993 |
| EP | 0711531 | 5/1996 |
| WO | WO-9739792 | 10/1997 |
| WO | WO-9801742 | 1/1998 |
| WO | WO-9842103 | 9/1998 |
| WO | WO-9946718 | 9/1999 |
| WO | WO-9955226 | 11/1999 |

OTHER PUBLICATIONS

"File History", for EP Patent Application No. 08163387.7, a divisional from EP Patent Application No. 00650198.5, corresponding to U.S. Appl. No. 09/441,405 (31 pages).

Auer, et al., "Paced Epimyocardial Electrograms for Noninvasive Rejection Monitoring After Heart Transplantation", *The Journal of Heart and Lung Transplantation*, vol. 15, No. 10, Oct. 1996, pp. 993-998.

Braunwald, E , "Heart Disease—A Testbook of Cardiovascular Medicine, W. B. Saunders Co., 1997, pp. 452-454".

(56) References Cited

OTHER PUBLICATIONS

Dunn, et al., "Telemedicine Links Patients in Sioux Lookout with Doctors in Toronto", *CMA Journal*, vol. 122, Feb. 23, 1980, pp. 484-487.

Hutten, et al., "Cardiac Telemonitoring by Integrating Pacemaker Telemetry within Worldwid Data Communication Systems", *Proceedings of 19th International Conference*, IEEE/EMBS, Chicago, IL, Oct. 30- Nov. 2, 1997, pp. 974-976.

Long, et al., "Differential Diagnosis Generation From a Causal Network With Probabilities", *Computers in Cardiology*, 1988, Proceedings, pp. 185-188, Washington DC, USA.

Magrabi, et al., "Web Based Longitudinal ECG Monitoring", *Proceedings of 20th Annual International Conference of the IEEE Engineering in Medicine and Biology Society*, vol. 20, No. 3, pp. 1155-1158 (1998).

Moody, , "Integration of Real-Time and Off-Line Clinical Data in the MIMIC Database", *Computers in Cardiology 1997 vol. 24*, pp. 585-588, Cambridge, MA USA.

Nelwan, et al., "Ubiquitous Access to Real-Time Patient Monitoring Data", *Computers in Cardiollogy.*, vol. 24, pp. 271-274 (1997).

Roberge, et al., "Basic and Applied Biomedical Engineering Building Blocks for Health Care", *1995 IEEE Engineering in Medicine and Biology 17th Annual Conference*, vol. 1, Montreal, Canada (Sep. 20-23, 1995).

Schreier, et al., "A Non-Invasive Rejection Monitoring System Based on Remote Analysis of Intramyocardial Electrograms from Heart Transplants", IEEE, pp. 35-36.

Vargas, Juan E., "Home-Based Monitoring of Cardiac Patients", *Dept. of Electr. & Comput. Eng.*, South Carolina Univ., Columbia, SC, Information Technology Applications in Biomedicine, Proceedings., 1998 IEEE International Conference, pp. 133-136 (May 16-17, 1998).

"File History", for co-owned U.S. Appl. No. 11/512,689, filed on Aug. 29, 2006, Issued as 8,092,382 on Jan. 10, 2012. (309 pages).

"File History", for co-owned U.S. Appl. No. 13/312,174, filed on Dec. 6, 2011, Issued as 8,369,937 on Feb. 5, 2013. (135 pages).

\* cited by examiner

| Physiological Measure | Time of Day | Sequence |
|---|---|---|
| Acidity (pH) Level (41) | 10/25/1999 14:00 | 1 |
| Arterial Carbon Dioxide Score (42) | 10/25/1999 14:00 | 2 |
| Arterial Oxygen Score (43) | 10/25/1999 14:00 | 3 |
| Atrial Electrical Activity (44) | 10/25/1999 14:00 | 4 |
| Blood Pressure (45) | 10/25/1999 14:00 | 5 |
| Body Temperature (46) | 10/25/1999 14:00 | 6 |
| BUN and Creatinine (47) | 10/25/1999 14:00 | 7 |
| Cardiac Injury Chemical Tests (48) | 10/25/1999 14:00 | 8 |
| Cardiac Output (49) | 10/25/1999 14:00 | 9 |
| Cardiovascular Pressures (50) | 10/25/1999 14:00 | 10 |
| CNS Blood Flow (51) | 10/25/1999 14:00 | 11 |
| CNS Injury Chemical Tests (52) | 10/25/1999 14:00 | 12 |
| Coronary Sinus Lactate Production (53) | 10/25/1999 14:00 | 13 |
| Glucose Level (54) | 10/25/1999 14:00 | 14 |
| Hematocrit (55) | 10/25/1999 14:00 | 15 |
| Hormonal Levels (56) | 10/25/1999 14:00 | 16 |
| Interventions Made (57) | 10/25/1999 14:00 | 17 |
| Left Ventricular Wall Motion Changes (58) | 10/25/1999 14:00 | 18 |
| Lung Injury Chemical Tests (59) | 10/25/1999 14:00 | 19 |
| Minute Ventilation (60) | 10/25/1999 14:00 | 20 |
| Mixed Venous Oxygen Score (61) | 10/25/1999 14:00 | 21 |
| Myocardial Blood Flow (62) | 10/25/1999 14:00 | 22 |
| Patient Activity Score (63) | 10/25/1999 14:00 | 23 |
| Patient Geographic Location (Altitude) (64) | 10/25/1999 14:00 | 24 |
| Posture (65) | 10/25/1999 14:00 | 25 |
| Potassium [K+] Level (66) | 10/25/1999 14:00 | 26 |
| PR Interval or AV Interval (67) | 10/25/1999 14:00 | 27 |
| Pulmonary Artery Diastolic Pressure Measure (68) | 10/25/1999 14:00 | 28 |
| Pulmonary Artery Systolic Pressure Measure (69) | 10/25/1999 14:00 | 29 |
| Pulmonary Measures (70) | 10/25/1999 14:00 | 30 |
| QRS Measures (71) | 10/25/1999 14:00 | 31 |
| QT Interval (72) | 10/25/1999 14:00 | 32 |
| Respiratory Rate (73) | 10/25/1999 14:00 | 33 |
| Serum Myocardial Creatinine Kinase (74) | 10/25/1999 14:00 | 34 |
| Serum Troponin (75) | 10/25/1999 14:00 | 35 |
| Sodium [Na+] Level (76) | 10/25/1999 14:00 | 36 |
| ST Segment Measures (77) | 10/25/1999 14:00 | 37 |
| ST-T Wave Measures (78) | 10/25/1999 14:00 | 38 |
| Success of Interventions Made (79) | 10/25/1999 14:00 | 39 |
| T Wave Measures (80) | 10/25/1999 14:00 | 40 |
| Temperature (81) | 10/25/1999 14:00 | 41 |
| Transthoracic Impedance (82) | 10/25/1999 14:00 | 42 |
| Ventilatory Tidal Volume (83) | 10/25/1999 14:00 | 43 |
| Ventricular Electrical Activity (84) | 10/25/1999 14:00 | 44 |
| Time of Day (85) | 10/25/1999 14:00 | 45 |

| Quality of Life (QOL) Measure | Time of Day | Sequence |
|---|---|---|
| Overall Health Wellness (96) | 10/25/1999 14:00 | 1 |
| Psychological State (97) | 10/25/1999 14:00 | 2 |
| Chest Discomfort (98) | 10/25/1999 14:00 | 3 |
| Location of Chest Discomfort (99) | 10/25/1999 14:00 | 4 |
| Palpitations (100) | 10/25/1999 14:00 | 5 |
| Shortness of Breath (101) | 10/25/1999 14:00 | 6 |
| Exercise Tolerance (102) | 10/25/1999 14:00 | 7 |
| Cough (103) | 10/25/1999 14:00 | 8 |
| Sputum Production (104) | 10/25/1999 14:00 | 9 |
| Sputum Color (105) | 10/25/1999 14:00 | 10 |
| Energy Level (106) | 10/25/1999 14:00 | 11 |
| Syncope (107) | 10/25/1999 14:00 | 12 |
| Near Syncope (108) | 10/25/1999 14:00 | 13 |
| Nausea (109) | 10/25/1999 14:00 | 14 |
| Diaphoresis (110) | 10/25/1999 14:00 | 15 |
| Time of Day (111) | 10/25/1999 14:00 | 16 |
|  |  |  |

Patient 1

| Set 0 |   |   |   | Set n-2 | Set n-1 | Set n |
|---|---|---|---|---|---|---|
| $X_0$ | • | • | • | $X_{n-2}$ | $X_{n-1}$ | $X_n$ |
| $Y_0$ | • | • | • | $Y_{n-2}$ | $Y_{n-1}$ | $Y_n$ |
| $Z_0$ | • | • | • | $Z_{n-2}$ | $Z_{n-1}$ | $Z_n$ |

*time →*

Patient 2

| Set 0 |   |   |   | Set n-2 | Set n-1 | Set n |
|---|---|---|---|---|---|---|
| $X_{0'}$ | • | • | • | $X_{n-2'}$ | $X_{n-1'}$ | $X_{n'}$ |
| $Y_{0'}$ | • | • | • | $Y_{n-2'}$ | $Y_{n-1'}$ | $Y_{n'}$ |
| $Z_{0'}$ | • | • | • | $Z_{n-2'}$ | $Z_{n-1'}$ | $Z_{n'}$ |

*time →*

Patient 3

| Set 0 |   |   |   | Set n-2 | Set n-1 | Set n |
|---|---|---|---|---|---|---|
| $X_{0''}$ | • | • | • | $X_{n-2''}$ | $X_{n-1''}$ | $X_{n''}$ |
| $Y_{0''}$ | • | • | • | $Y_{n-2''}$ | $Y_{n-1''}$ | $Y_{n''}$ |
| $Z_{0''}$ | • | • | • | $Z_{n-2''}$ | $Z_{n-1''}$ | $Z_{n''}$ |

*time →*

357

SYSTEM AND METHOD FOR PRIORITIZING MEDICAL CONDITIONS

CROSS-REFERENCE TO RELATED APPLICATIONS

This patent application is a divisional of U.S. Pat. No. 8,369,937, issued Feb. 5, 2013, which is a continuation of U.S. Pat. No. 8,092,382, issued Jan. 10, 2012, which is a divisional of U.S. Pat. No. 7,117,028, issued Oct. 3, 2006, which is a continuation of U.S. Pat. No. 6,951,539, issued Oct. 4, 2005, which is a continuation of U.S. Pat. No. 6,834,203, issued Dec. 21, 2004, which is a continuation of U.S. Pat. No. 6,440,066, issued Aug. 27, 2002, the disclosures of which are incorporated by reference, and the priority filing dates of which are claimed.

FIELD OF THE INVENTION

The present invention relates in general to automated multiple near-simultaneous health disorder diagnosis and analysis, and, in particular, to an automated collection and analysis patient care system and method for ordering and prioritizing multiple health disorders to identify an index disorder.

BACKGROUND OF THE INVENTION

The rising availability of networked digital communications means, particularly wide area networks (WANs), including public information internetworks such as the Internet, have made possible diverse opportunities for providing traditional storefront- or office-bound services through an automated and remote distributed system arrangement. For example, banking, stock trading, and even grocery shopping can now be performed on-line over the Internet. However, some forms of services, especially health care services which include disease diagnosis and treatment, require detailed and personal knowledge of the consumer/patient. The physiological data that would allow assessment of a disease has traditionally been obtained through the physical presence of the individual at the physician's office or in the hospital.

Presently, important physiological measures can be recorded and collected for patients equipped with an external monitoring or therapeutic device, or via implantable device technologies, or recorded manually by the patient. If obtained frequently and regularly, these recorded physiological measures can provide a degree of disease detection and prevention heretofore unknown. For instance, patients already suffering from some form of treatable heart disease often receive an implantable pulse generator (IPG), cardiovascular or heart failure monitor, therapeutic device, or similar external wearable device, with which rhythm and structural problems of the heart can be monitored and treated. These types of devices are useful for detecting physiological changes in patient conditions through the retrieval and analysis of telemetered signals stored in an on-board, volatile memory. Typically, these devices can store more than thirty minutes of per heartbeat data recorded on a per heartbeat, binned average basis, or on a derived basis from which can be measured or derived, for example, atrial or ventricular electrical activity, minute ventilation, patient activity score, cardiac output score, mixed venous oxygen score, cardiovascular pressure measures, and the like. However, the proper analysis of retrieved telemetered signals requires detailed medical subspecialty knowledge in the area of heart disease, such as by cardiologists and cardiac electrophysiologists.

Alternatively, these telemetered signals can be remotely collected and analyzed using an automated patient care system. One such system is described in a related, commonly assigned U.S. Pat. No. 6,312,378, issued Nov. 6, 2001, the disclosure of which is incorporated herein by reference. A medical device adapted to be implanted in an individual patient records telemetered signals that are then retrieved on a regular, periodic basis using an interrogator or similar interfacing device. The telemetered signals are downloaded via an internetwork onto a network server on a regular, e.g., daily, basis and stored as sets of collected measures in a database along with other patient care records. The information is then analyzed in an automated fashion and feedback, which includes a patient status indicator, is provided to the patient.

While such an automated system can serve as a valuable tool in providing remote patient care, an approach to systematically correlating and analyzing the raw collected telemetered signals, as well as manually collected physiological measures, through applied medical knowledge to accurately diagnose, order and prioritize multiple near-simultaneous health disorders, such as, by way of example, congestive heart failure, myocardial ischemia, respiratory insufficiency, and atrial fibrillation, is needed. As a case in point, a patient might develop pneumonia that in turn triggers the onset of myocardial ischemia that in turn leads to congestive heart failure that in turn causes the onset of atrial fibrillation that in turn exacerbates all three preceding conditions. The relative relationship of the onset and magnitude of each disease measure abnormality has direct bearing on the optimal course of therapy. Patients with one or more pre-existing diseases often present with a confusing array of problems that can be best sorted and addressed by analyzing the sequence of change in the various physiological measures monitored by the device.

One automated patient care system directed to a patient-specific monitoring function is described in U.S. Pat. No. 5,113,869 ('869) to Nappholz et al. The '869 patent discloses an implantable, programmable electrocardiography (ECG) patient monitoring device that senses and analyzes ECG signals to detect ECG and physiological signal characteristics predictive of malignant cardiac arrhythmias. The monitoring device can communicate a warning signal to an external device when arrhythmias are predicted. However, the Nappholz device is limited to detecting ventricular tachycardias. Moreover, the ECG morphology of malignant cardiac tachycardias is well established and can be readily predicted using on-board signal detection techniques. The Nappholz device is patient specific and is unable to automatically take into consideration a broader patient or peer group history for reference to detect and consider the progression or improvement of cardiovascular disease. Additionally, the Nappholz device is unable to automatically self-reference multiple data points in time and cannot detect disease regression. Also, the Nappholz device must be implanted and cannot function as an external monitor. Finally, the Nappholz device is incapable of tracking the cardiovascular and cardiopulmonary consequences of any rhythm disorder.

Consequently, there is a need for an approach for remotely ordering and prioritizing multiple, related medical diseases and disorders using an automated patient collection and analysis patient care system. Preferably, such an approach would identify a primary or index disorder for diagnosis and treatment, while also aiding in the management of secondary disorders that arise as a consequence of the index event.

There is a further need for an automated, distributed system and method capable of providing medical health care services to remote patients via a distributed communications means, such as a WAN, including the Internet. Preferably, such a system and method should be capable of monitoring objective "hard" physiological measures and subjective "soft" quality of life and symptom measures and correlating the two forms of patient health care data to order, prioritize and identify disorders and disease.

SUMMARY OF THE INVENTION

The present invention provides a system and method for remotely ordering and prioritizing multiple, near-simultaneous health disorders using an automated collection and analysis patient care system. The various physiological measures of individual patients are continuously monitored using implantable, external, or manual medical devices and the recorded physiological measures are downloaded on a substantially regular basis to a centralized server system. Derived measures are extrapolated from the recorded measures. As an adjunct to the device-recorded measures, the patients may regularly submit subjective, quality of life and symptom measures to the server system to assist identifying a change in health condition and to correlate with objective health care findings. Changes in patient status are determined by observing differences between the various recorded, derived and quality of life and symptom measures over time. Any changes in patient status are correlated to multiple disorder candidates having similar abnormalities in physiological measures for identification of a primary index disorder candidate.

In one embodiment of the technology disclosed herein a method for providing an index disorder in automated patient care is taught. A set of device measures is stored in a database. Quantitative health care data indicators in the database are provided, where the indicators were regularly recorded by a medical device for a patient under automated patient care. Collected device measures are retrieved with a processor. An index disorder is identified through derived measure determination and statistical calculation with a processor.

An embodiment of the present invention is an automated collection and analysis patient care system and method for ordering and prioritizing multiple health disorders to identify an index disorder. A plurality of monitoring sets is retrieved from a database. Each of the monitoring sets include stored measures relating to patient information recorded and derived on a substantially continuous basis. A patient status change is determined by comparing at least one stored measure from each of the monitoring sets to at least one other stored measure with both stored measures relating to the same type of patient information. Each patient status change is ordered in temporal sequence from least recent to most recent. A plurality of health disorder candidates categorized by quantifiable physiological measures of pathophysiologies indicative of each respective health disorder are evaluated and the health disorder candidate with the pathophysiology most closely matching those patient status changes which occurred least recently is identified as the index disorder, that is, the inciting disorder.

The present invention provides a capability to detect and track subtle trends and incremental changes in recorded patient medical information for automated multiple near-simultaneous health disorder diagnosis and analysis. When coupled with an enrollment in a remote patient monitoring service having the capability to remotely and continuously collect and analyze external or implantable medical device measures, automated multiple health disorder diagnosis and analysis ordering and prioritizing become feasible.

Another benefit is improved predictive accuracy from the outset of patient care when a reference baseline is incorporated into the automated diagnosis.

A further benefit is an expanded knowledge base created by expanding the methodologies applied to a single patient to include patient peer groups and the overall patient population. Collaterally, the information maintained in the database could also be utilized for the development of further predictive techniques and for medical research purposes.

Yet a further benefit is the ability to hone and improve the predictive techniques employed through a continual reassessment of patient therapy outcomes and morbidity rates.

Other benefits include an automated, expert system approach to the cross-referral, consideration, and potential finding or elimination of other diseases and health disorders with similar or related etiological indicators.

Still other embodiments of the present invention will become readily apparent to those skilled in the art from the following detailed description, wherein is described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

BRIEF DESCRIPTION OF THE DRAWINGS

FIG. 2 is a database table showing, by way of example, a partial record view of device and derived measures set records for remote patient care stored as part of a patient care record in the database of the system of FIG. 1;

FIG. 3 is a database table showing, by way of example, a partial record view of quality of life and symptom measures set records for remote patient care stored as part of a patient care record in the database of the system of FIG. 1;

FIG. 6 is a record view showing, by way of example, a set of partial patient care records stored in the database of the system of FIG. 1;

DETAILED DESCRIPTION

Figure 1:
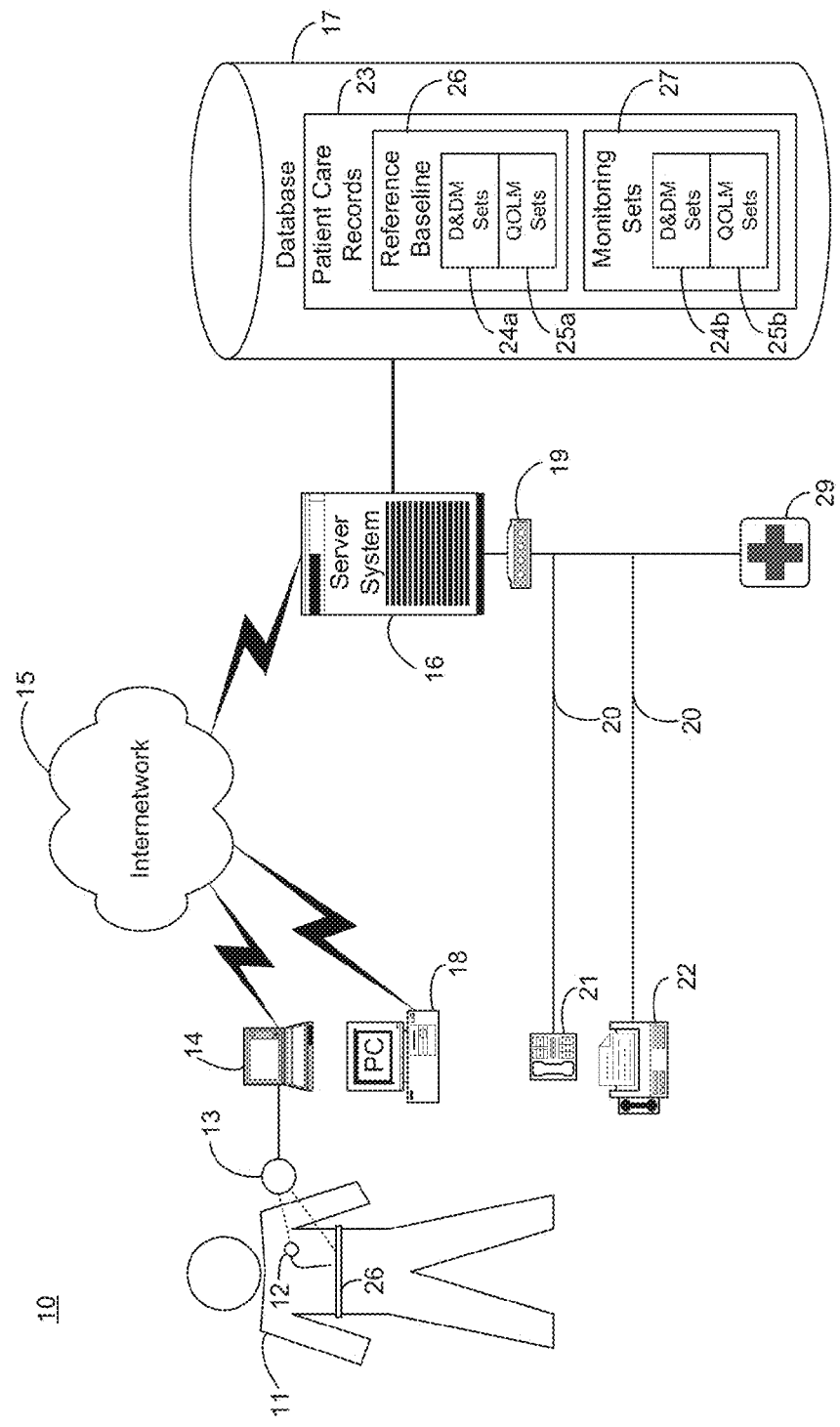
FIG. 1 is a block diagram showing an automated collection and analysis patient care system for ordering and prioritizing multiple health disorders in accordance with the present invention.

FIG. 1 is a block diagram showing an automated collection and analysis patient care system 10 for ordering and prioritizing multiple health disorders in accordance with the present invention. An exemplary automated collection and analysis patient care system suitable for use with the present invention is disclosed in the related, commonly assigned U.S. Pat. No. 6,312,378, issued Nov. 6, 2001, the disclosure of which is incorporated herein by reference. Preferably, an individual patient 11 is a recipient of an implantable medical device 12, such as, by way of example, an IPG, cardiovascular or heart failure monitor, or therapeutic device, with a set of leads extending into his or her heart and electrodes implanted throughout the cardiopulmonary system. Alternatively, an external monitoring or therapeutic medical device 26, a subcutaneous monitor or device inserted into other organs, a cutaneous monitor, or even a manual physiological measurement device, such as an electrocardiogram or heart rate monitor, could be used. The implantable medical device 12 and external medical device 26 include circuitry for recording into a short-term, volatile memory telemetered signals stored for later retrieval, which become part of a set of device and derived measures, such as described below, by way of example, with reference to FIG. 2. Exemplary implantable medical devices suitable for use in the present invention include the Discovery line of pacemakers, manufactured by Guidant Corporation, Indianapolis, Ind., and the Gem line of ICDs, manufactured by Medtronic Corporation, Minneapolis, Minn.

The telemetered signals stored in the implantable medical device 12 are preferably retrieved upon the completion of an initial observation period and subsequently thereafter on a continuous, periodic (daily) basis, such as described in the related, commonly assigned U.S. Pat. No. 6,221,011, issued Apr. 24, 2001, the disclosure of which is incorporated herein by reference. A programmer 14, personal computer 18, or similar device for communicating with an implantable medical device 12 can be used to retrieve the telemetered signals. A magnetized reed switch (not shown) within the implantable medical device 12 closes in response to the placement of a wand 13 over the site of the implantable medical device 12. The programmer 14 sends programming or interrogating instructions to and retrieves stored telemetered signals from the implantable medical device 12 via RF signals exchanged through the wand 13. Similar communication means are used for accessing the external medical device 26. Once downloaded, the telemetered signals are sent via an internetwork 15, such as the Internet, to a server system 16 which periodically receives and stores the telemetered signals as device measures in patient care records 23 in a database 17, as further described below, by way of example, with reference to FIG. 2. An exemplary programmer 14 suitable for use in the present invention is the Model 2901 Programmer Recorder Monitor, manufactured by Guidant Corporation, Indianapolis, Ind.

The patient 11 is remotely monitored by the server system 16 via the internetwork 15 through the periodic receipt of the retrieved device measures from the implantable medical device 12 or external medical device 26. The patient care records 23 in the database 17 are organized into two identified sets of device measures: an optional reference baseline 26 recorded during an initial observation period and monitoring sets 27 recorded subsequently thereafter. The monitoring measures sets 27 are periodically analyzed and compared by the server system 16 to indicator thresholds 204 (shown in FIG. 5 below) corresponding to quantifiable physiological measures of pathophysiologies indicative of multiple, near-simultaneous disorders, as further described below with reference to FIG. 5. As necessary, feedback is provided to the patient 11. By way of example, the feedback includes an electronic mail message automatically sent by the server system 16 over the internetwork 15 to a personal computer 18 (PC) situated for local access by the patient 11. Alternatively, the feedback can be sent through a telephone interface device 19 as an automated voice mail message to a telephone 21 or as an automated facsimile message to a facsimile machine 22, both also situated for local access by the patient 11. Moreover, simultaneous notifications can also be delivered to the patient's physician, hospital, or emergency medical services provider 29 using similar feedback means to deliver the information.

The server system 10 can consist of either a single computer system or a cooperatively networked or clustered set of computer systems. Each computer system is a general purpose, programmed digital computing device consisting of a central processing unit (CPU), random access memory (RAM), non-volatile secondary storage, such as a hard drive or CD ROM drive, network interfaces, and peripheral devices, including user interfacing means, such as a keyboard and display. Program code, including software programs, and data are loaded into the RAM for execution and processing by the CPU and results are generated for display, output, transmittal, or storage, as is known in the art.

The database 17 stores patient care records 23 for each individual patient to whom remote patient care is being provided. Each patient care record 23 contains normal patient identification and treatment profile information, as well as medical history, medications taken, height and weight, and other pertinent data (not shown). The patient care records 23 consist primarily of two sets of data: device and derived measures (D&DM) sets 24a, 24b and quality of life (QOL) and symptom measures sets 25a, 25b, the organization and contents of which are further described below with respect to FIGS. 2 and 3, respectively. The device and derived measures sets 24a, 24b and quality of life and symptom measures sets 25a, 25b can be further logically categorized into two potentially overlapping sets. The reference baseline 26 is a special set of device and derived reference measures sets 24a and quality of life and symptom measures sets 25a recorded and determined during an initial observation period. Monitoring sets 27 are device and derived measures sets 24b and quality of life and symptom measures sets 25b recorded and determined thereafter on a regular, continuous basis. Other forms of database organization and contents are feasible.

The implantable medical device 12 and, in a more limited fashion, the external medical device 26, record patient medical information on a regular basis. The recorded patient information is downloaded and stored in the database 17 as part of a patient care record 23. Further patient information can be derived from the recorded patient information, as is known in the art. FIG. 2 is a database table showing, by way of example, a partial record view 40 of device and derived measures set records 41-85 for remote patient care stored as part of a patient care record in the database 17 of the system of FIG. 1. Each record 41-85 stores physiological measures, the time of day and a sequence number, non-exclusively. The physiological measures can include a snapshot of telemetered signals data which were recorded by the implantable medical device 12 or the external medical device 26, for instance, on per heartbeat, binned average or derived basis; measures derived from the recorded device measures; and manually collected information, such as obtained through a patient medical history interview or questionnaire. The time of day records the time and date at which the physiological measure was recorded. Finally, the sequence number indicates the order in which the physiological measures are to be processed. Other types of collected, recorded, combined, or derived measures are possible, as is known in the art.

The device and derived measures sets 24a, 24b (shown in FIG. 1), along with quality of life and symptom measures sets 25a, 25b, as further described below with reference to FIG. 3, are continuously and periodically received by the server system 16 as part of the on-going patient care monitoring and analysis function. These regularly collected data sets are collectively categorized as the monitoring sets 27 (shown in FIG. 1). In addition, select device and derived measures sets 24a and quality of life and symptom measures sets 25a can be designated as a reference baseline 26 at the outset of patient care to improve the accuracy and meaningfulness of the serial monitoring sets 27. Select patient information is collected, recorded, and derived during an initial period of observation or patient care, such as described in the related, commonly assigned U.S. Pat. No. 6,221,011, issued Apr. 24, 2001, the disclosure of which is incorporated herein by reference.

As an adjunct to remote patient care through the monitoring of measured physiological data via the implantable medical device 12 or external medical device 26, quality of life and symptom measures sets 25a can also be stored in the database 17 as part of the reference baseline 26, if used, and the monitoring sets 27. A quality of life measure is a semi-quantitative self-assessment of an individual patient's physical and emotional well being and a record of symptoms, such as provided by the Duke Activities Status Indicator. These scoring systems can be provided for use by the patient 11 on the personal computer 18 (shown in FIG. 1) to record his or her quality of life scores for both initial and periodic download to the server system 16. FIG. 3 is a database table showing, by way of example, a partial record view 95 of quality of life and symptom measures set records 96-111 for remote patient care stored as part of a patient care record in the database 17 of the system of FIG. 1. Similar to the device and derived measures set records 41-85, each record 96-111 stores the quality of life (QOL) measure, the time of day and a sequence number, non-exclusively.

Other types of quality of life and symptom measures are possible, such as those indicated by responses to the Minnesota Living with Heart Failure Questionnaire described in E. Braunwald, ed., "Heart Disease—A Textbook of Cardiovascular Medicine," pp. 452-454, W.B. Saunders Co. (1997), the disclosure of which is incorporated herein by reference. Similarly, functional classifications based on the relationship between symptoms and the amount of effort required to provoke them can serve as quality of life and symptom measures, such as the New York Heart Association (NYHA) classifications I, II, III and IV, also described in Ibid.

The patient may also add non-device quantitative measures, such as the six-minute walk distance, as complementary data to the device and derived measures sets 24a, 24b and the symptoms during the six-minute walk to quality of life and symptom measures sets 25a, 25b.

Figure 4:
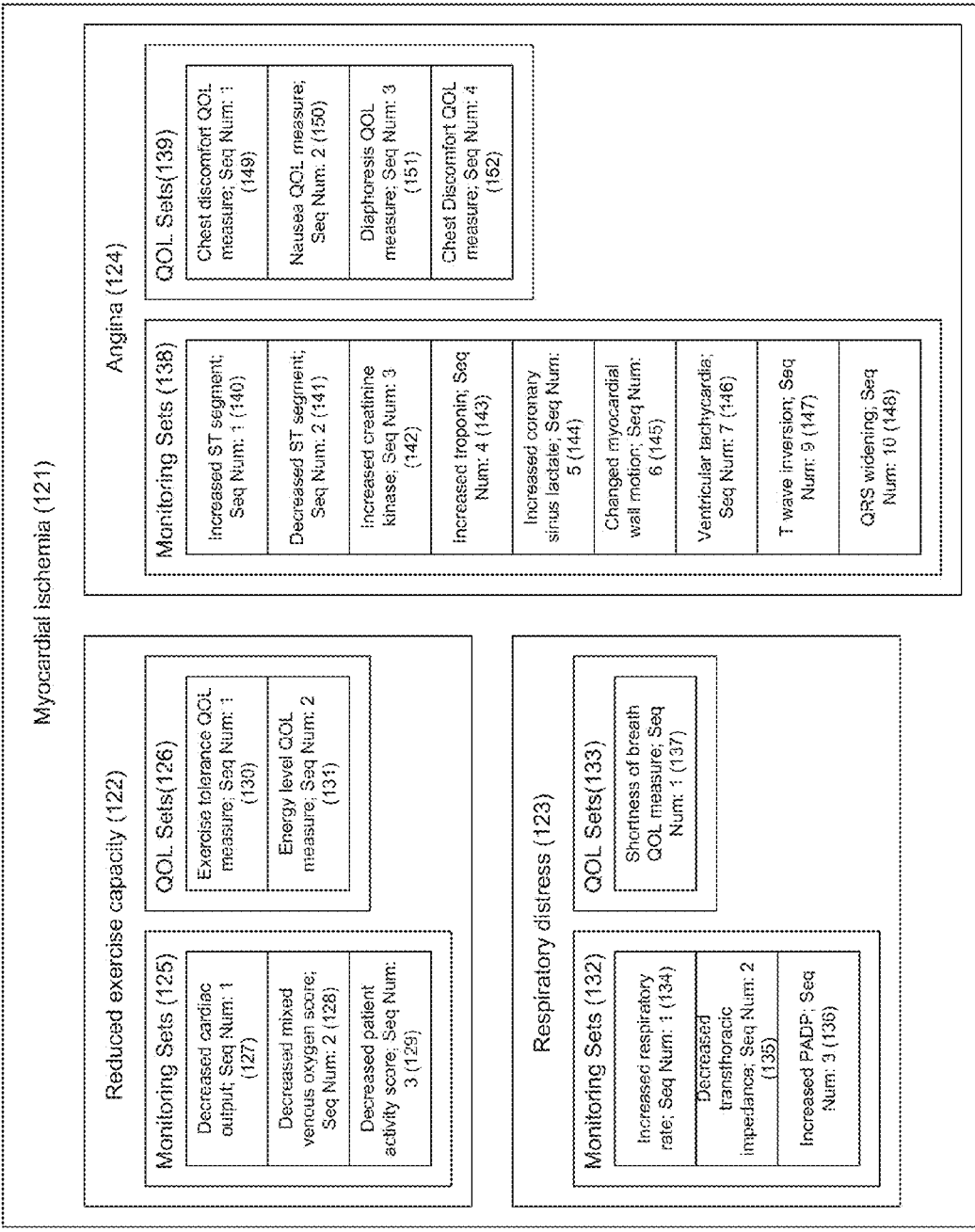
FIG. 4 is a database schema showing, by way of example, the organization of a symptomatic event ordering set record for remote patient care stored as part of a symptomatic event ordering set for use in the system of FIG. 1.

On a periodic basis, the patient information stored in the database 17 is evaluated and, if medically significant changes in patient wellness are detected and medical disorders are identified. The sequence of symptomatic events is crucial. FIG. 4 is a database schema showing, by way of example, the organization of a symptomatic event ordering set record 120 for remote patient care stored as part of a symptomatic event ordering set 205 (shown in FIG. 5 below) for use in the system of FIG. 1. By way of example, the record 120 stores and categorizes the general symptomatic event markers for myocardial ischemia 121 into event marker sets: reduced exercise capacity 122, respiratory distress 123, and angina 124. In turn, each of the event marker sets 122-124 contain monitoring sets 125, 132, 138 and quality of life (QOL) sets 126, 133, 139, respectively. Finally, each respective monitoring set and quality of life set contains a set of individual symptomatic events which together form a set of related and linked dependent measures. Here, the monitoring set 125 for reduced exercise capacity 122 contains decreased cardiac output 127, decreased mixed venous oxygen score 128, and decreased patient activity score 129 and the quality of life set 126 contains exercise tolerance quality of life measure 130 and energy level quality of life measure 131. Each symptomatic event contains a sequence number (Seq Num) indicating the order in which the symptomatic event will be evaluated, preferably proceeding from highly indicative to least indicative. For example, reduced exercise capacity in congestive heart failure is characterized by decreased cardiac output, as opposed to, say, reduced exercise capacity in primary pulmonary insufficiency where cardiac output is likely to be normal. An absolute limit of cardiac output, indexed for weight, can therefore serve as an a priori marker of congestive heart failure in the absence of intravascular volume depletion, i.e., low pulmonary artery diastolic pressure. Consequently, the markers of reduced exercise capacity in congestive heart failure order cardiac output as the indicator having the highest priority with a sequence number of "1." Quality of life symptomatic events are similarly ordered.

Figure 5:
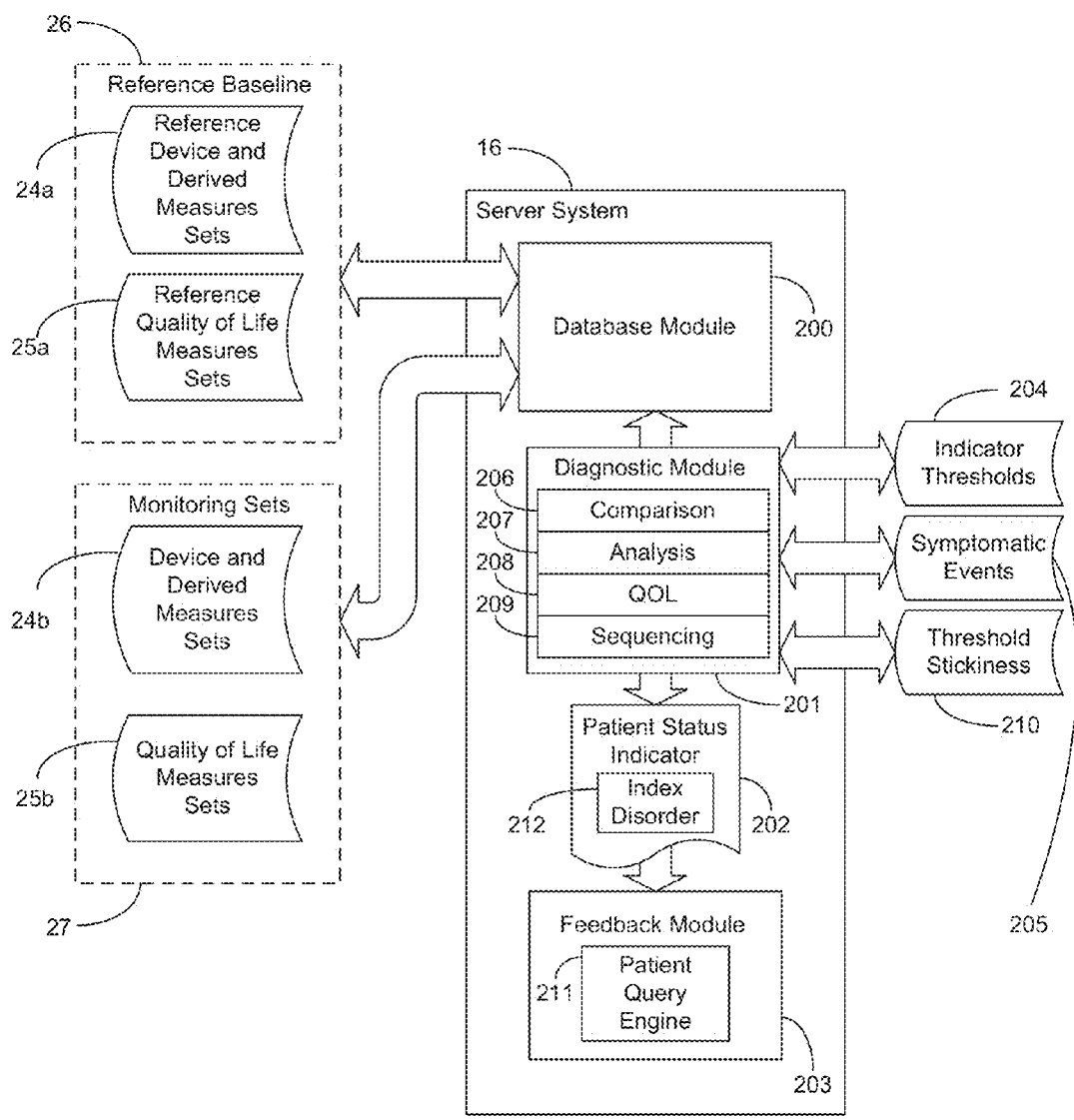
FIG. 5 is a block diagram showing the software modules of the server system of the system of FIG. 1.

FIG. 5 is a block diagram showing the software modules of the server system 16 of the system 10 of FIG. 1. Each module is a computer program written as source code in a conventional programming language, such as the C or Java programming languages, and is presented for execution by the CPU of the server system 16 as object or byte code, as is known in the art. The various implementations of the source code and object and byte codes can be held on a computer-readable storage medium or embodied on a transmission medium in a carrier wave. The server system 16 includes three primary software modules, database module 200, diagnostic module 201, and feedback module 203, which perform integrated functions as follows.

First, the database module 200 organizes the individual patient care records 23 stored in the database 17 (shown in FIG. 1) and efficiently stores and accesses the reference baseline 26, monitoring sets 27, and patient care data maintained in those records. Any type of database organization could be utilized, including a flat file system, hierarchical database, relational database, or distributed database, such as provided by database vendors, such as Oracle Corporation, Redwood Shores, Calif.

Next, the diagnostic module 201 determines the ordering and prioritization of multiple near-simultaneous disorders to determine an index disorder 212, that is, the inciting disorder, based on the comparison and analysis of the data measures from the reference baseline 26 and monitoring sets 27. The diagnostic module includes four modules: comparison module 206, analysis module 207, quality of life module 208, and sequencing module 209. The comparison module 206 compares recorded and derived measures retrieved from the reference baseline 26, if used, and monitoring sets 27 to indicator thresholds 204. The comparison module 206 also determines changes between recorded and derived measures retrieved from the reference baseline 26, if used, and monitoring sets 27 to determine the occurrence of a symptomatic event using the symptomatic event ordering set 205. The database 17 stores individual patient care records 23 for patients suffering from various health disorders and diseases for which they are receiving remote patient care. For purposes of comparison and analysis by the comparison module 206, these records can be categorized into peer groups containing the records for those patients suffering from similar disorders and diseases, as well as being viewed in reference to the overall patient population. The definition of the peer group can be progressively refined as the overall patient population grows. To illustrate, FIG. 6 is a record view showing, by way of example, a set of partial patient care records stored in the database 17 for three patients, Patient 1, Patient 2, and Patient 3. For each patient, three sets of peer measures, X, Y, and Z, are shown. Each of the measures, X, Y, and Z, could be either collected or derived measures from the reference baseline 26, if used, and monitoring sets 27.

The same measures are organized into time-based sets with Set 0 representing sibling measures made at a reference time t=0. Similarly, Set n-2, Set n-1 and Set n each represent sibling measures made at later reference times t=n-2, t=n-1 and t=n, respectively. Thus, for a given patient, such as Patient 1, serial peer measures, such as peer measure $X_0$ through $X_n$, represent the same type of patient information monitored over time. The combined peer measures for all patients can be categorized into a health disorder- or disease-matched peer group. The definition of disease-matched peer group is a progressive definition, refined over time as the number of monitored patients grows and the features of the peer group become increasingly well-matched and uniform. Measures representing different types of patient information, such as measures $X_0$, $Y_0$, and $Z_0$, are sibling measures. These are measures which are also measured over time, but which might have medically significant meaning when compared to each other within a set for an individual patient.

The comparison module 206 performs two basic forms of comparison. First, individual measures for a given patient can be compared to other individual measures for that same patient (self-referencing). These comparisons might be peer-to-peer measures projected over time, for instance, $X_n$, $X_{n-1}$, $X_{n-2}$, ... $X_0$, or sibling-to-sibling measures for a single snapshot, for instance, $X_n$, $Y_n$, and $Z_n$, or projected over time, for instance, $X_n$, $Y_n$, $Z_n$, $X_{n-1}$, $Y_{n-1}$, $Z_{n-1}$, $X_{n-2}$, $Y_{n-2}$, $Z_{n-2}$, ... $X_0$, $Y_0$, $Z_0$. Second, individual measures for a given patient can be compared to other individual measures for a group of other patients sharing the same disorder- or disease-specific characteristics (peer group referencing) or to the patient population in general (population referencing). Again, these comparisons might be peer-to-peer measures projected over time, for instance, $X_n$, $X_{n'}$, $X_{n''}$, $X_{n-1}$, $X_{n-1'}$, $X_{n-1''}$, $X_{n-2}$, $X_{n-2'}$, $X_{n-2''}$ ... $X_0$, $X_{0'}$, $X_{0''}$, or comparing the individual patient's measures to an average from the group. Similarly, these comparisons might be sibling-to-sibling measures for single snapshots, for instance, $X_n$, $X_{n'}$, $X_{n''}$, $Y_n$, $Y_{n'}$, $Y_{n''}$, and $Z_n$, $Z_{n'}$, $Z_{n''}$, or projected over time, for instance, $X_n$, $X_{n'}$, $X_{n''}$, $Y_n$, $Y_{n'}$, $Y_{n''}$, $Z_n$, $Z_{n'}$, $Z_{n''}$, $X_{n-1}$, $X_{n-1'}$, $X_{n-1''}$, $Y_{n-1}$, $Y_{n-1'}$, $Y_{n-1''}$, $Z_{n-1}$, $Z_{n-1'}$, $Z_{n-1''}$, $X_{n-2}$, $X_{n-2'}$, $X_{n-2''}$, $Y_{n-2}$, $Y_{n-2'}$, $Y_{n-2''}$, $Z_{n-2}$, $Z_{n-2'}$, $Z_{n-2''}$ ... $X_0$, $X_{0'}$, $X_{0''}$, $Y_0$, $Y_{0'}$, $Y_{0''}$, and $Z_0$, $Z_{0'}$, $Z_{0''}$. Other forms of comparisons are feasible, including multiple disease diagnoses for diseases exhibiting similar physiological measures or which might be a secondary disease candidate.

Figure 7:
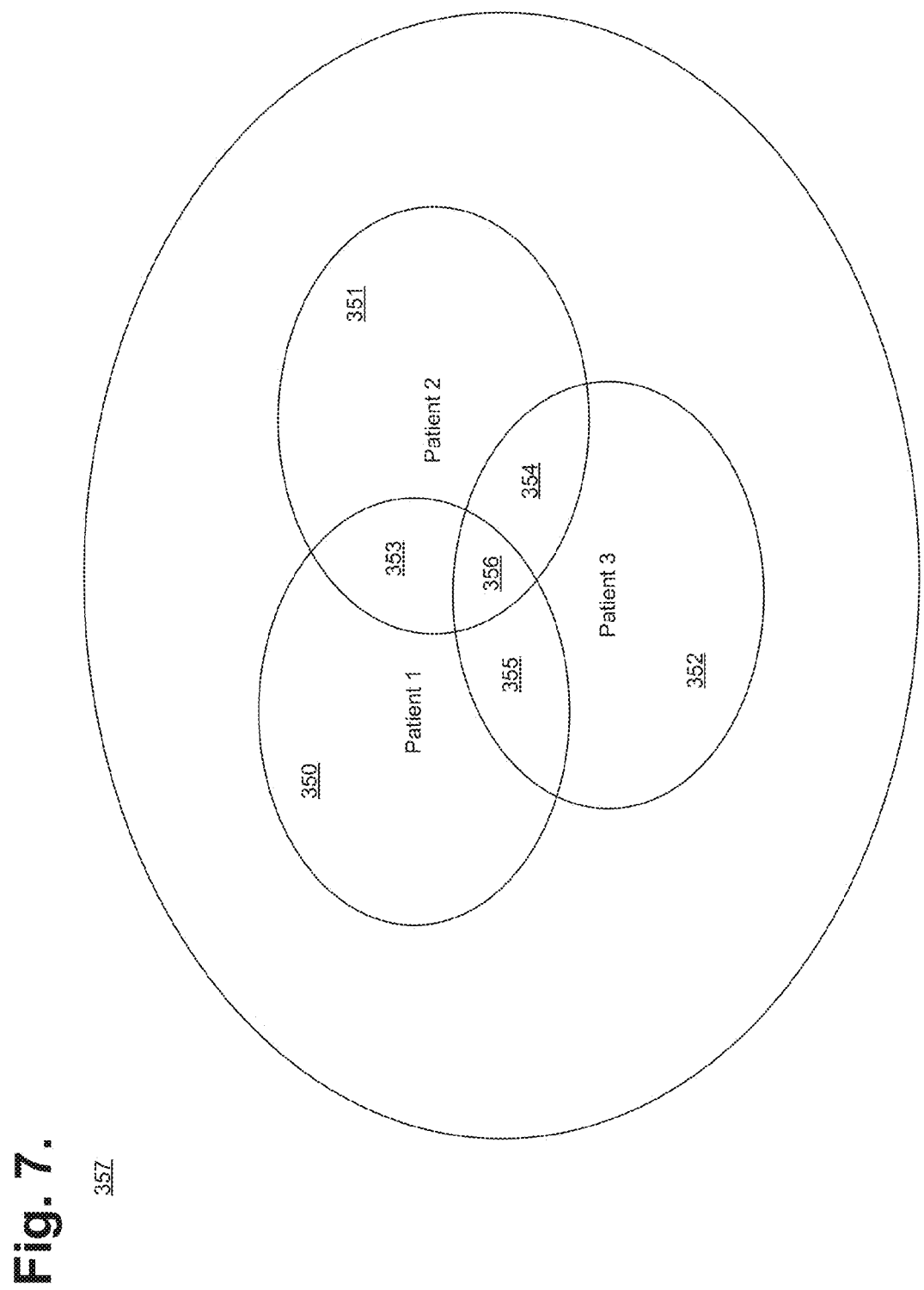
FIG. 7 is a Venn diagram showing, by way of example, peer group overlap between the partial patient care records of FIG. 6.

FIG. 7 is a Venn diagram showing, by way of example, peer group overlap between the partial patient care records 23 of FIG. 1. Each patient care record 23 includes characteristics data 350, 351, 352, including personal traits, demographics, medical history, and related personal data, for patients 1, 2 and 3, respectively. For example, the characteristics data 350 for patient 1 might include personal traits which include gender and age, such as male and an age between 40-45; a demographic of resident of New York City; and a medical history consisting of anterior myocardial infraction, congestive heart failure and diabetes. Similarly, the characteristics data 351 for patient 2 might include identical personal traits, thereby resulting in partial overlap 353 of characteristics data 350 and 351. Similar characteristics overlap 354, 355, 356 can exist between each respective patient. The overall patient population 357 would include the universe of all characteristics data. As the monitoring population grows, the number of patients with personal traits matching those of the monitored patient will grow, increasing the value of peer group referencing. Large peer groups, well matched across all monitored measures, will result in a well known natural history of disease and will allow for more accurate prediction of the clinical course of the patient being monitored. If the population of patients is relatively small, only some traits 356 will be uniformly present in any particular peer group. Eventually, peer groups, for instance, composed of 100 or more patients each, would evolve under conditions in which there would be complete overlap of substantially all salient data, thereby forming a powerful core reference group for any new patient being monitored with similar characters.

Referring back to FIG. 5, the analysis module 207 orders any patient status changes resulting from differences between physiological measures and identifies an index disorder 212, as further described below with reference to FIGS. 8A-8B. Similarly, the quality of life module 208 compares quality of life and symptom measures set 25a, 25b from the reference baseline 26 and monitoring sets 27, the results of which are incorporated into the comparisons performed by the analysis module 13, in part, to either refute or support the findings based on physiological "hard" data. The sequencing module 209 prioritizes patient changes in accordance with pre-defined orderings, if used, or as modified by quality of life and symptom measures.

Finally, the feedback module 203 provides automated feedback to the individual patient based, in part, on the patient status indicator 202 generated by the diagnostic module 201.

In addition, the feedback module 203 determines whether any changes to interventive measures are appropriate based on threshold stickiness ("hysteresis") 210. The threshold stickiness 210 can limit the diagnostic measures to provide a buffer against transient, non-trending and non-significant fluctuations in the various collected and derived measures in favor of more certainty in diagnosis. As described above, the feedback could be by electronic mail or by automated voice mail or facsimile. The feedback can also include normalized voice feedback, such as described in the related, commonly assigned U.S. Pat. No. 6,203,495, issued Mar. 20, 2001, the disclosure of which is incorporated herein by reference.

In a further embodiment of the present invention, the feedback module 203 includes a patient query engine 211, which enables the individual patient 11 to interactively query the server system 16 regarding the diagnosis, therapeutic maneuvers, and treatment regimen. Similar patient query engines 211 can be found in interactive expert systems for diagnosing medical conditions. Using the personal computer 18 (shown in FIG. 1), the patient can have an interactive dialogue with the automated server system 16, as well as human experts as necessary, to self assess his or her medical condition. Such expert systems are well known in the art, an example of which is the MYCIN expert system developed at Stanford University and described in Buchanan, B. & Shortlife, E., "RULE-BASED EXPERT SYSTEMS. The MYCIN Experiments of the Stanford Heuristic Programming Project," Addison-Wesley (1984). The various forms of feedback described above help to increase the accuracy and specificity of the reporting of the quality of life and symptomatic measures.

Figure 8A:
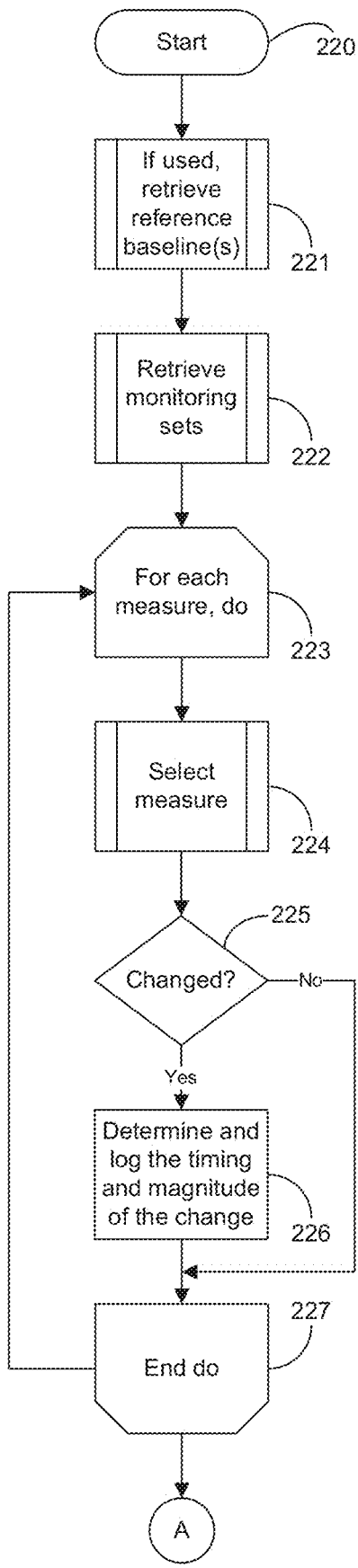
FIGS. 8A-8B are flow diagrams showing a method for ordering and prioritizing multiple health disorders using an automated collection and analysis patient care system in accordance with the present invention
Figure 8B:
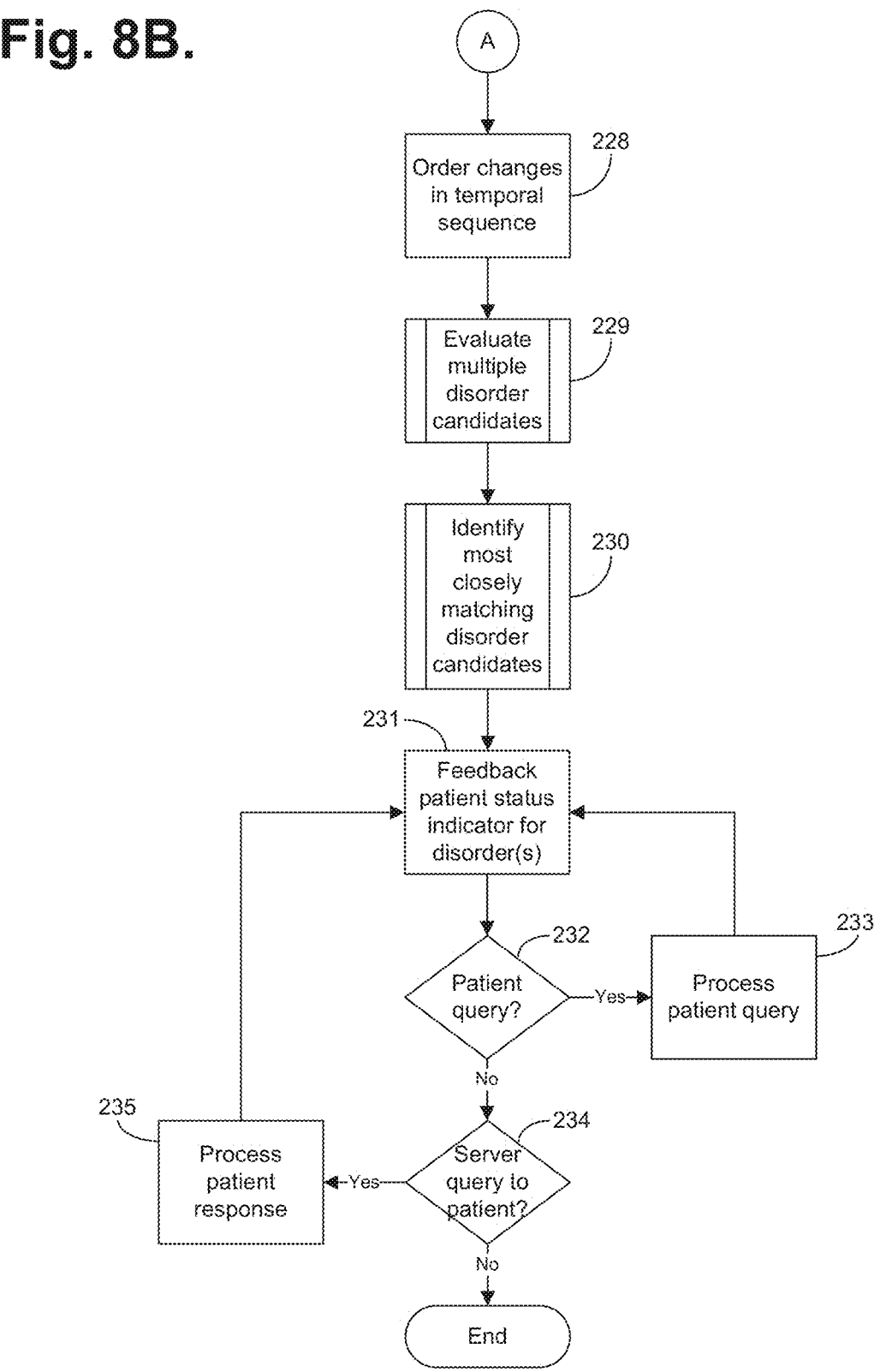

FIGS. 8A-8B are flow diagrams showing a method for ordering and prioritizing multiple health disorders 220 to identify an index disorder 212 (shown in FIG. 5) using an automated collection and analysis patient care system 10 in accordance with the present invention. A primary purpose of this method is to determine what happened first to sort through multiple near-simultaneously-occurring disorders. For example, congestive heart failure can lead to myocardial insufficiency and vice versa. Moreover, congestive heart failure can complicate preexisting borderline pulmonary insufficiency. Similarly, when individuals have borderline or subclinical congestive heart failure or myocardial ischemia, primary pulmonary insufficiency, for example, an exacerbation of chronic bronchitis, can lead to fulminant congestive heart failure, myocardial ischemia, or both. Atrial fibrillation can complicate all of the above-noted disorders, either as a result of or as a precipitant of one of the foregoing disorders.

The sequence of the events resulting from changes in physiological measures, as may be corroborated by quality of life and symptom measures, is crucial. In patients with more than one disease, certain physiological measures are the key to identifying the index disorder; however, these same physiological measures might not be uniquely abnormal to any particular disorder. Consequently, a diagnosis depending upon these particular non-diagnostic physiological measures will be more dependent upon the ordering of changes or measure creep than the physiological measure value itself For example, cardiac output 49 (shown in FIG. 2) or its derivatives can decrease in congestive heart failure, myocardial ischemia, respiratory insufficiency, or atrial fibrillation. However, decreased cardiac output in myocardial ischemia would be preceded by an abnormality of ST elevation (ST segment measures 77), T-wave inversion (T wave measures 79), troponin increase (serum troponin 74), wall motion abnormality onset (left ventricular wall motion changes 58), increased coronary sinus lactate production 53, and possibly QRS widening (as a marker of myocardial ischemia) (QRS measures 70).

Similarly, decreased cardiac output in respiratory insufficiency would be preceded by other physiological measures, which, although not as diagnostic as myocardial ischemia, can include, for example, elevation in respiratory rate 72, elevation in minute ventilation 60, elevation in tidal volume (derived from minute ventilation 60 and respiratory rate 72), increase in transthoracic impedance 81 consistent with increased aeration of the lungs, decrease in QT interval 71 (or other surrogate for increase in temperature), spikes in the activity sensor 63 or pulmonary artery pressures 66, 68 as markers of cough 103, decrease in arterial partial pressure of oxygen 43, and decreases in arterial partial pressure of carbon dioxide 42 in probable association with low or normal pulmonary artery diastolic pressure 67. Once pulmonary insufficiency onsets, the subsequent fall in arterial oxygen pressure may be enough to trigger myocardial ischemia, in the case of a patient with borderline coronary artery disease, or to trigger congestive heart failure, in the case of a patient with borderline left ventricular dysfunction. However, these disorders would be identified as secondary disorders with the aid of the present invention.

Note that the foregoing interrelationships between the respective physiological measures for diagnosing and treating congestive heart failure, myocardial ischemia, respiratory insufficiency and atrial fibrillation are merely illustrative and not exhaustive. Moreover, other heretofore unidentified disorders can also share such interrelationships, as is known in the art, to cover, non-specified disorder diagnostics, such as for diabetes, hypertension, sleep-apnea, stroke, anemia, and so forth.

Thus, the method begins by retrieving the reference baseline 26 (block 221) and monitoring sets 27 (block 222) from the database 17, as further described below with reference to FIGS. 9 and 10, respectively. Each measure in the device and derived measures sets 24a, 24b (shown in FIG. 1) and quality of life and symptom measures sets 25a, 25b, if used, is iteratively processed (blocks 223-227). These measures are obtained from the monitoring sets 27 and, again if used, the reference baseline 26. During each iteration loop, a measure is selected (block 224), as further described below with reference to FIG. 11. If the measure has changed (block 225), the timing and magnitude of the change is determined and logged (block 226). Iterative processing (blocks 223-227) continues until all measures have been selected at which time any changes are ordered in temporal sequence (block 228) from least recent to most recent. Next, multiple disorder candidates are evaluated (block 229) and the most closely matching disorder candidates, including a primary or index disorder and any secondary disorders, are identified (block 230), as further described below respectively in FIGS. 12A-12B and 13A-13B. A patient status indicator 202 for any identified disorders, including the primary or index disorder 212 (shown in FIG. 5), is provided (block 231) to the patient regarding physical well-being, disease prognosis, including any determinations of disease onset, progression, regression, or status quo, and other pertinent medical and general information of potential interest to the patient.

Finally, in a further embodiment, if the patient submits a query to the server system 16 (block 232), the patient query is interactively processed by the patient query engine (block 233). Similarly, if the server elects to query the patient (block 234), the server query is interactively processed by the server query engine (block 235). The method then terminates if no further patient or server queries are submitted.

In the described embodiment, both the time at which a change occurred and the relative magnitude of the change are utilized for indexing the diagnosis. In addition, related measures are linked into dependent sets of measures, preferably by disorder and principal symptom findings (e.g., as shown in FIG. 4), such that any change in one measure will automatically result in the examination of the timing and magnitude in any changes in the related measures. For example, ST segment changes (measure 76 shown in FIG. 2) can fluctuate slightly with or without severe consequences in patient condition. A 0.5 SD change in ST segment, for instance, is generally considered modest when not tied to other physiological measure changes. However, a 0.5 SD ST segment change followed by a massive left ventricular wall motion change 58 can indicate, for example, left anterior descending coronary artery occlusion. The magnitude of change therefore can help determine the primacy of the pertinent disorder and the timing and sequence of related changes can help categorize the clinical severity of the inciting event.

Also, an adjustable time window can be used to detect measure creep by widening the time period over which a change in physiological measure can be observed. For example, mean cardiac output 49 may appear unchanging over a short term period of observation, for instance, one week, but might actually be decreasing subtly from month-to-month marking an insidious, yet serious disease process. The adjustable time window allows such subtle, trending changes to be detected.

Similarly, a clinically reasonable time limit can be placed on the adjustable time window as an upper bound. The length of the upper bound is disease specific. For example, atrial fibrillation preceded by congestive heart failure by 24 hours is correlative; however, atrial fibrillation preceded by congestive heart failure one year earlier will likely not be considered an inciting factor without more closely temporally linked changes. Similarly, congestive heart failure secondary to atrial fibrillation can occur more gradually than congestive heart failure secondary to myocardial ischemia. The upper bound therefore serves to limit the scope of the time period over which changes to physiological measures are observed and adjusted for disease-specific diagnostic purposes.

Figure 9:
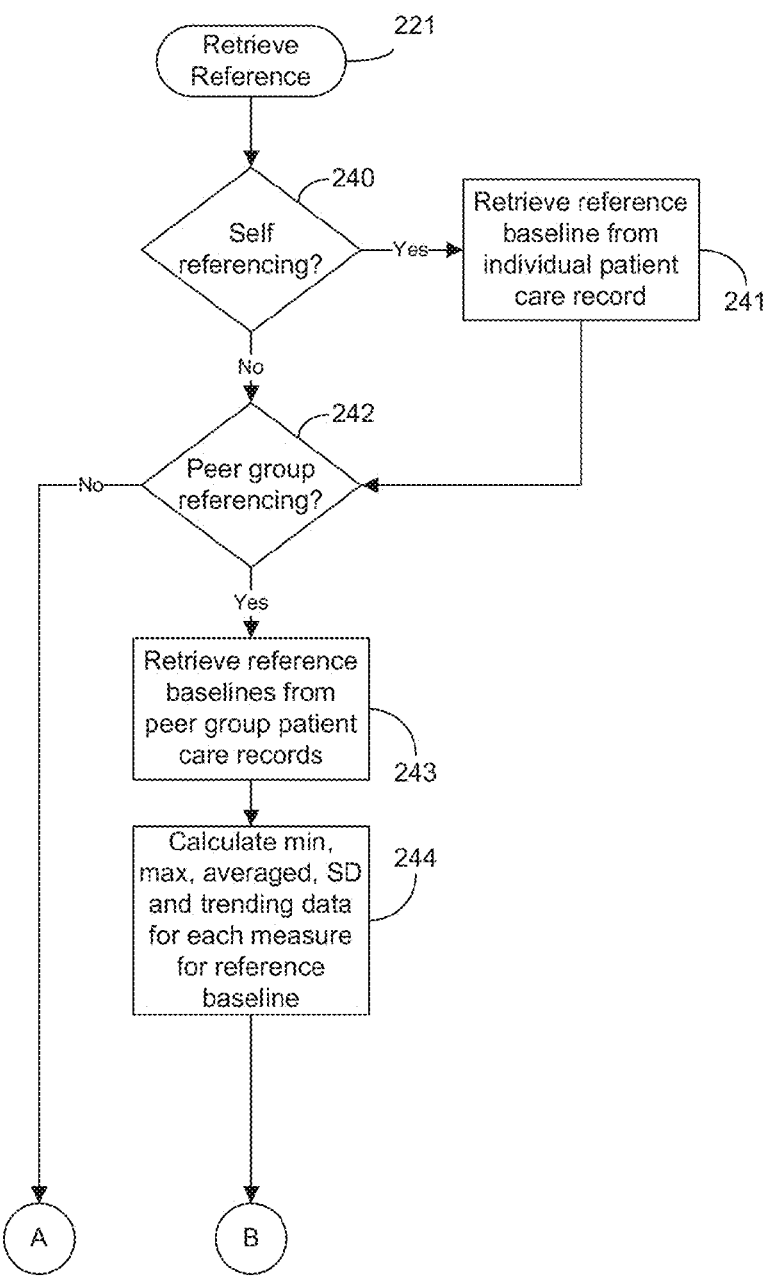
FIG. 9 is a flow diagram showing the routine for retrieving reference baseline sets for use in the method of FIGS. 8A-8B.
Figure 9:
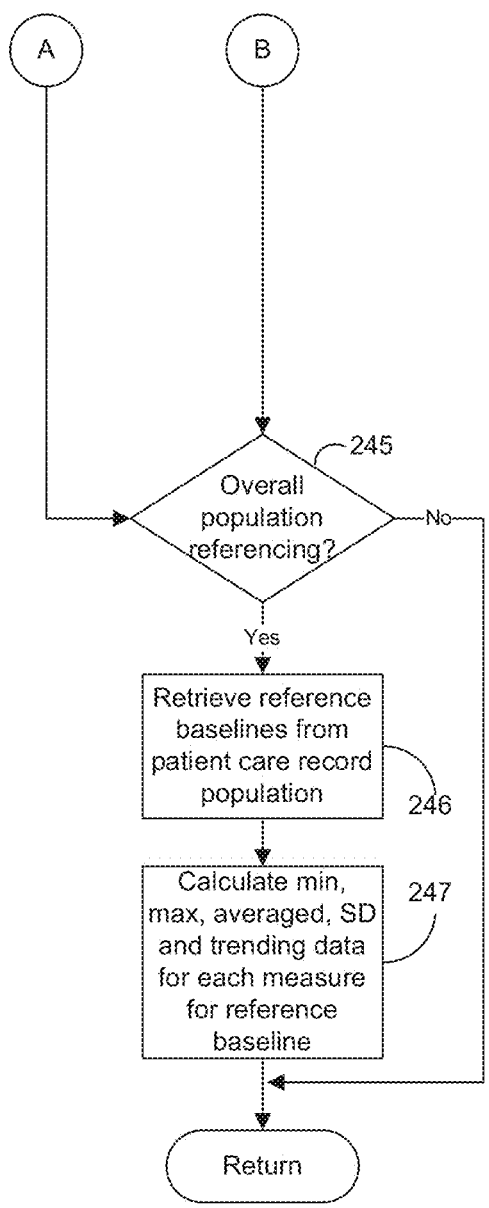

FIG. 9 is a flow diagram showing the routine for retrieving reference baseline sets 221 for use in the method of FIGS. 8A-8B. The purpose of this routine is to retrieve the appropriate reference baseline sets 26, if used, from the database 17 based on the types of comparisons being performed. First, if the comparisons are self referencing with respect to the measures stored in the individual patient care record 23 (block 240), the reference device and derived measures set 24a and reference quality of life and symptom measures set 25a, if used, are retrieved for the individual patient from the database 17 (block 241). Next, if the comparisons are peer group referencing with respect to measures stored in the patient care records 23 for a health disorder- or disease-specific peer group (block 242), the reference device and derived measures set 24a and reference quality of life and symptom measures set 25a, if used, are retrieved from each patient care record 23 for the peer group from the database 17 (block 243). Minimum, maximum, averaged, standard deviation (SD), and trending data for each measure from the reference baseline 26 for the peer group is then calculated (block 244). Finally, if the comparisons are population referencing with respect to measures stored in the patient care records 23 for the overall patient population (block 245), the reference device and derived measures set 24a and reference quality of life and symptom measures set 25a, if used, are retrieved from each patient care record 23 from the database 17 (block 246). Minimum, maximum, averaged, standard deviation, and trending data for each measure from the reference baseline 26 for the peer group is then calculated (block 247). The routine then returns.

Figure 10:
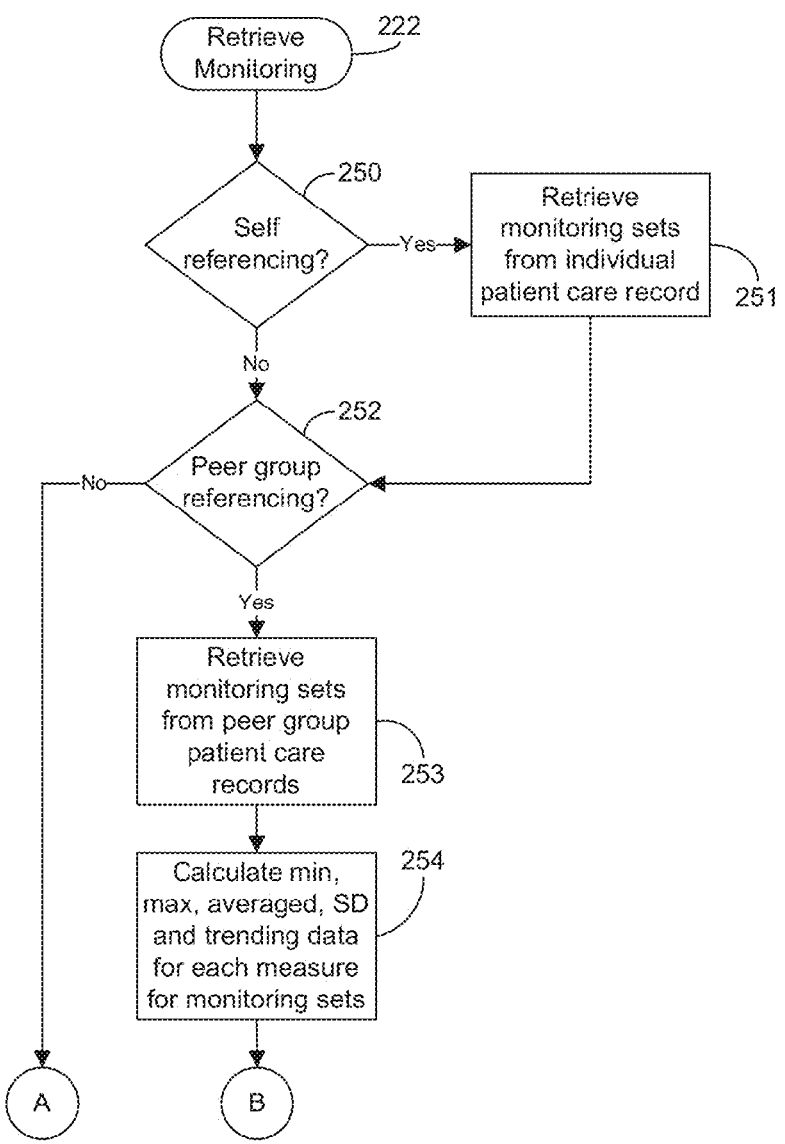
FIG. 10 is a flow diagram showing the routine for retrieving monitoring sets for use in the method of FIGS. 8A-8B.
Figure 10:
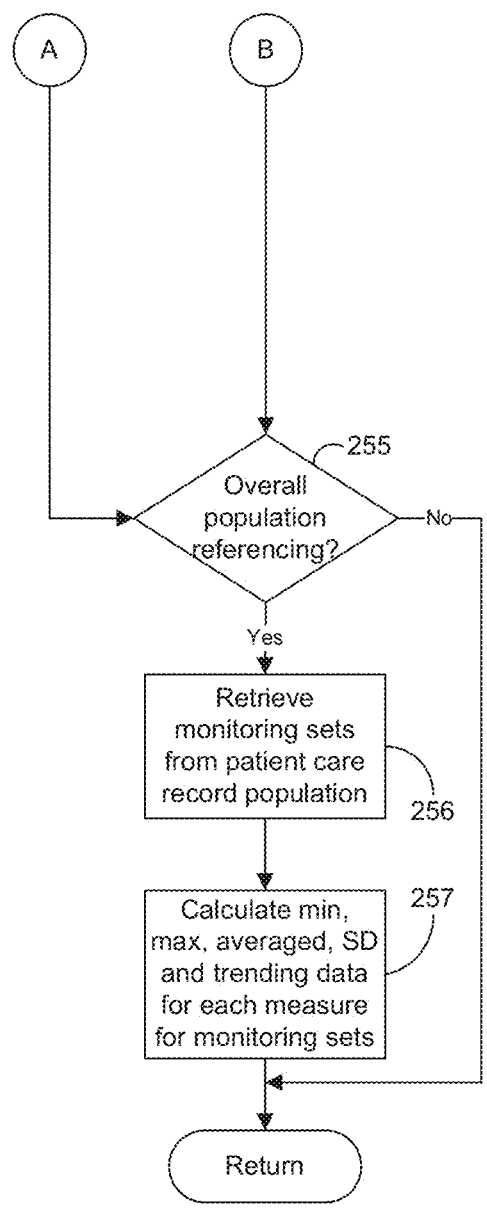

FIG. 10 is a flow diagram showing the routine for retrieving monitoring sets 222 for use in the method of FIGS. 8A-8B. The purpose of this routine is to retrieve the appropriate monitoring sets 27 from the database 17 based on the types of comparisons being performed. First, if the comparisons are self referencing with respect to the measures stored in the individual patient care record 23 (block 250), the device and derived measures set 24b and quality of life and symptom measures set 25b, if used, are retrieved for the individual patient from the database 17 (block 251). Next, if the comparisons are peer group referencing with respect to measures stored in the patient care records 23 for a health disorder- or disease-specific peer group (block 252), the device and derived measures set 24b and quality of life and symptom measures set 25b, if used, are retrieved from each patient care record 23 for the peer group from the database 17 (block 253). Minimum, maximum, averaged, standard deviation, and trending data for each measure from the monitoring sets 27 for the peer group is then calculated (block 254). Finally, if the comparisons are population referencing with respect to measures stored in the patient care records 23 for the overall patient population (block 255), the device and derived measures set 24b and quality of life and symptom measures set 25b, if used, are retrieved from each patient care record 23 from the database 17 (block 256). Minimum, maximum, averaged, standard deviation, and trending data for each measure from the monitoring sets 27 for the peer group is then calculated (block 257). The routine then returns.

Figure 11:
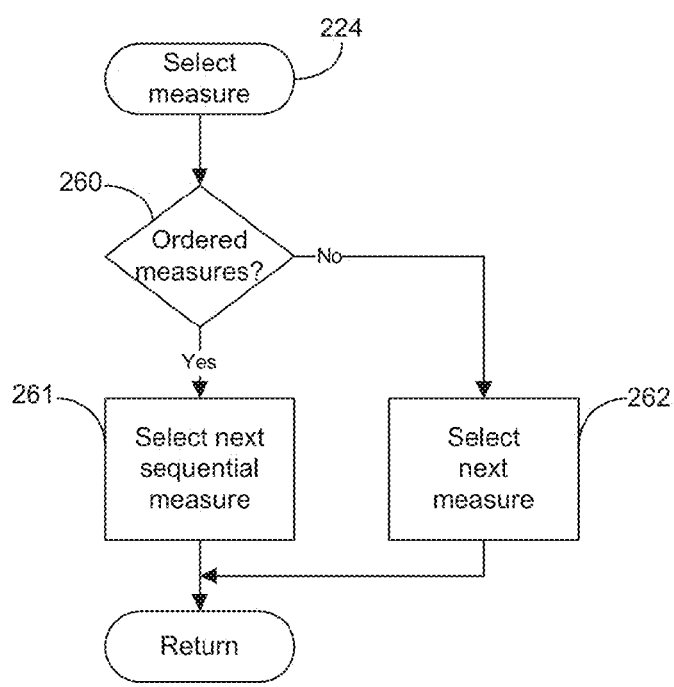
FIG. 11 is a flow diagram showing the routine for selecting a measure for use in the method of FIGS. 8A-8B.

FIG. 11 is a flow diagram showing the routine for selecting a measure 224 for use in the method of FIGS. 8A-8B. The purpose of this routine is to select a measure from the device and derived measures sets 24a, 24b or quality of life and symptom measures sets 25a, 25b in an appropriate order. Thus, if the measures are ordered in a pre-defined sequence (block 260), the next sequential measure is selected for comparison in the method of FIGS. 8A-8B (block 261). Otherwise, the next measure appearing in the respective measures set is selected (block 262). The routine then returns.

Figure 12A:
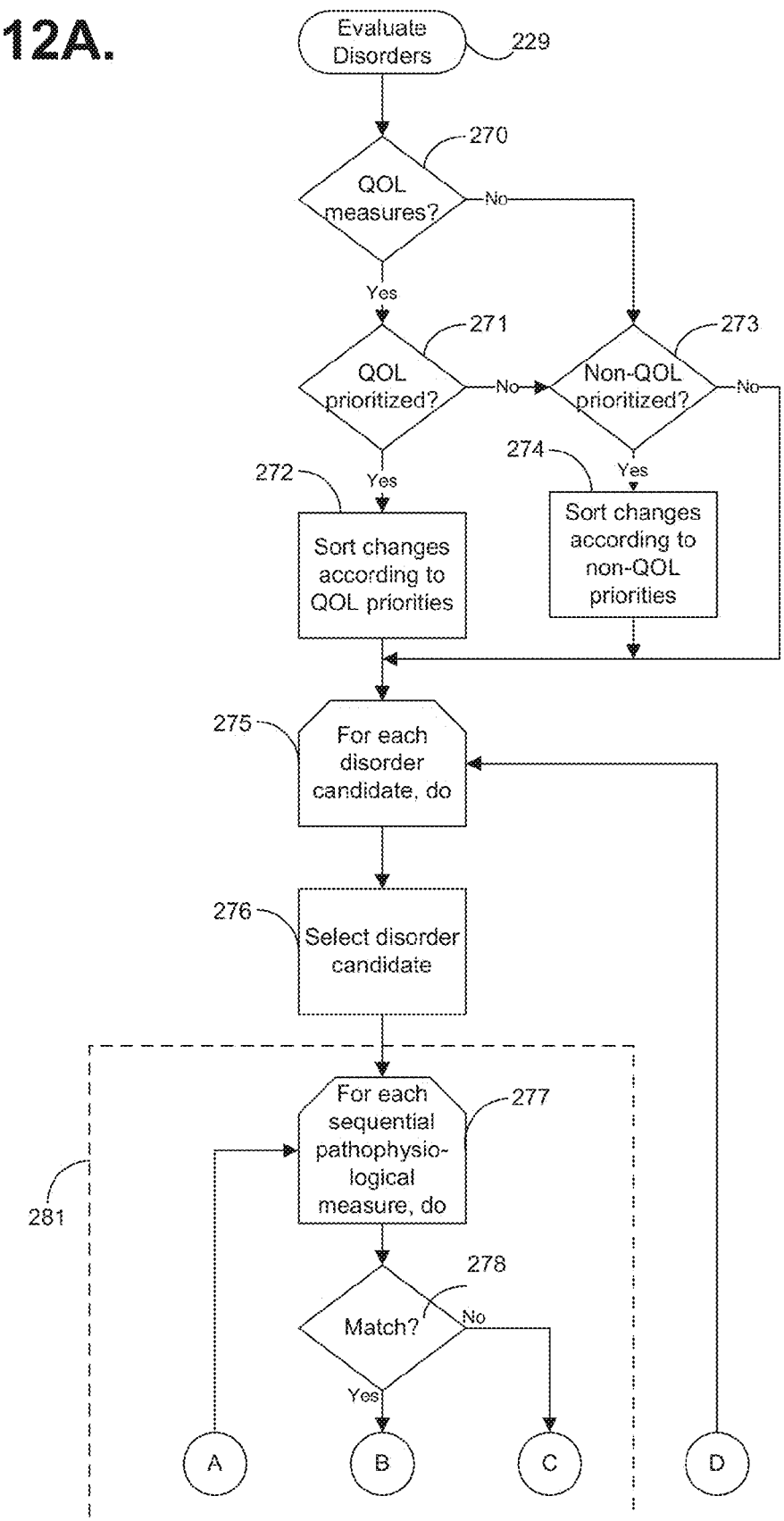
FIGS. 12A-12B are flow diagrams showing the routine for evaluating multiple disorder candidates for use in the method of FIGS. 8A-8B.
Figure 12B:
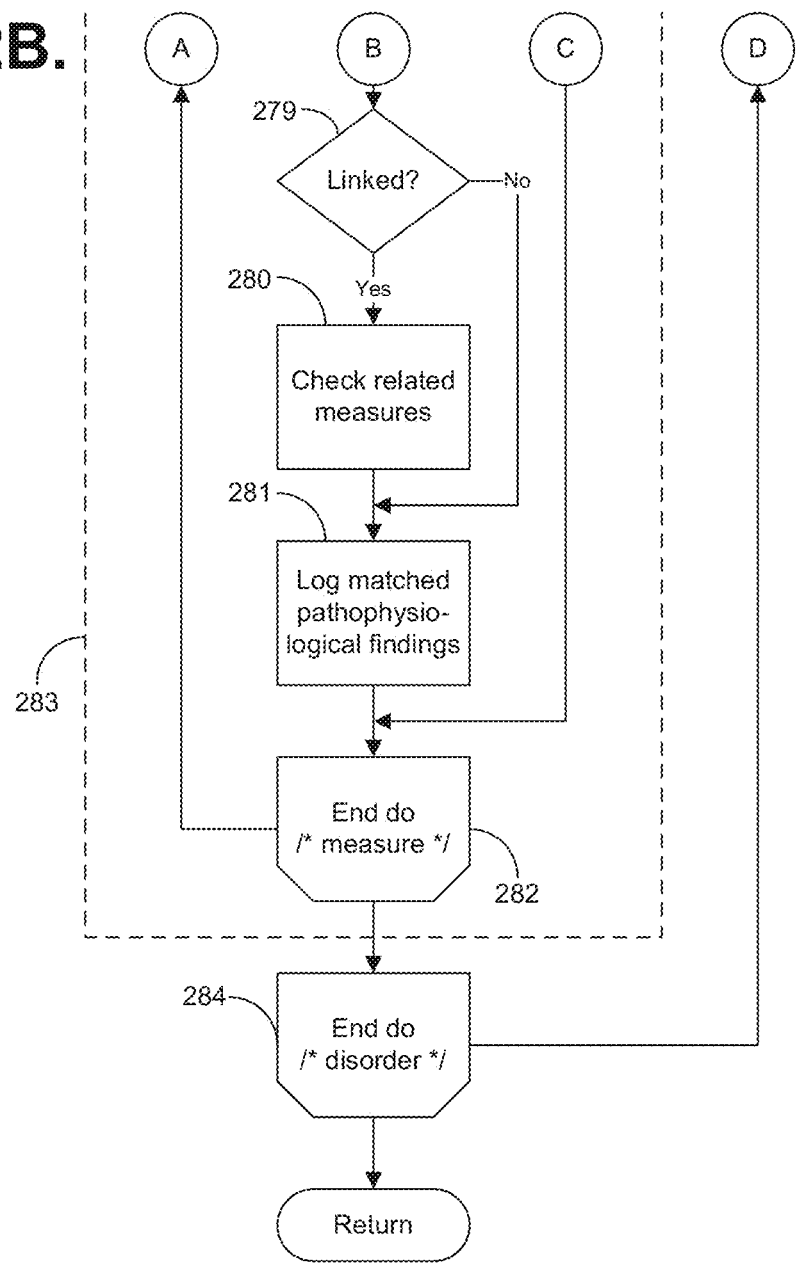

FIGS. 12A-12B are flow diagrams showing the routine for evaluating multiple disorder candidates 229 for use in the method of FIGS. 8A-8B. The purpose of this routine is to generate a log of findings based on comparisons of patient status changes to the various pathophysiological markers characteristic of each of the multiple, near-simultaneous disorders. Quality of life and symptom measures can be used in two ways. First, changes in a quality of life and symptom measures can serve as a starting point in diagnosing a disorder. For instance, shortness of breath 93 (shown in FIG. 3) can serve as a marker of respiratory distress congestive heart failure. Second, quality of life and symptom measures can corroborate disorder findings. In the described embodiment, the use of quality of life and symptom measures as a diagnostic starting point is incorporated into the analysis by prioritizing the importance of related physiological measure changes based on the least recent quality of life measure change. For example, if shortness of breath 93 followed the corresponding physiological changes for respiratory distress congestive heart failure, that is, decreased cardiac output 127 (shown in FIG. 4), decreased mixed venous oxygen score 128, and decreased patient activity score 129, would be assigned a higher priority than the other physiological measures. Similarly, in the described embodiment, certain physiological measures can also be assigned a higher priority independent of any changes to the quality of life and symptom measures.

Thus, if quality of life and symptom measures are included in the diagnostic process (block 270) and the related physiological measures are prioritized based on quality of life changes (block 271), the changes in physiological measures are sorted according to the quality of life-assigned priorities (block 272). Alternatively, if quality of life and symptom measures are not being used (block 270) or the changes in physiological measures are not assigned quality of life priorities (block 271), the physiological changes could still be independently prioritized (block 273). If so, the physiological measures are sorted according to the non-quality of life assigned-priorities (block 274).

Next, each of the multiple disorder candidates and each measure in their respective sets of physiological measures, including any linked measures, and, if used, quality of life and symptom measures, are iteratively processed in a pair of nested processing loops (blocks 275-284 and 277-282, respectively). Other forms of flow control are feasible, including recursive processing. Each disorder candidate is iteratively processed in the outer processing loop (blocks 275-284). During each outer processing loop, a disorder candidate is selected (block 276) and each of the physiological measures, and quality of life and symptom measures, if used, are iteratively processed in the inner processing loop (blocks 277-282). Each measure is assigned a sequence number, such as shown, by way of example, in each symptomatic event ordering set records 121-152 (shown in FIG. 4) for a principal symptom finding of the disorder candidate. The measures are evaluated in sequential order for timing and magnitude changes (block 278). If the measure is linked to other related measures (block 279), the related measures are also checked for timing and magnitude changes (block 280). Any matched pathophysiological findings are logged (block 281). The operations of evaluating and matching pathophysiological measures (box 283) for diagnosing congestive heart failure, myocardial infarction, respiratory distress, and atrial fibrillation are described in related, commonly assigned U.S. Pat. No. 6,336,903, entitled "Automated Collection And Analysis Patient Care System And Method For Diagnosing And Monitoring Congestive Heart Failure And Outcomes Thereof," issued Jan. 8, 2002; U.S. Pat. No. 6,368,284, entitled "Automated Collection And Analysis Patient Care System And Method For Diagnosing And Monitoring Myocardial Ischemia And Outcomes Thereof," issued Apr. 9, 2002; U.S. Pat. No. 6,398,728, entitled "Automated Collection And Analysis Patient Care System And Method For Diagnosing And Monitoring Respiratory Insufficiency And Outcomes Thereof," issued Jun. 4, 2002; and U.S. Pat. No. 6,411,840, entitled "Automated Collection And Analysis Patient Care System And Method For Diagnosing And Monitoring The Outcomes Of Atrial Fibrillation," issued Jun. 25, 2002, the disclosures of which are incorporated herein by reference. Note the evaluation and matching of pathophysiological measures 283 can also encompass disease worsening and improvement.

Iterative processing of measures (blocks 277-282) continues until all pathophysiological measures of the disorder have been evaluated, whereupon the next disorder candidate is selected. Iterative processing of disorders (blocks 275-284) continues until all disorders have been selected, after which the routine returns.

Figure 13A:
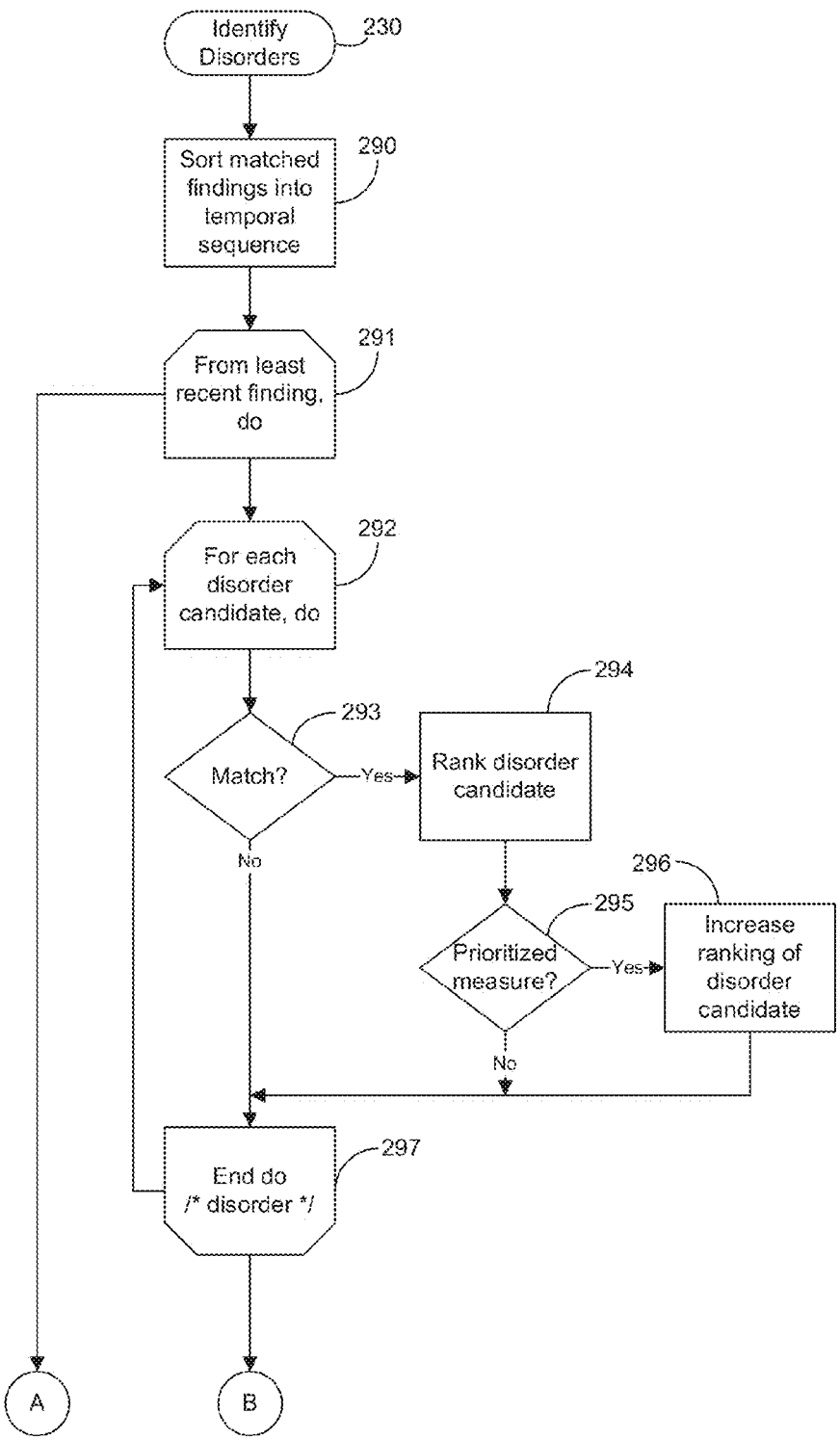
FIGS. 13A-13B are flow diagrams showing the routine for identifying disorder candidates for use in the method of FIGS. 8A-8B.
Figure 13B:
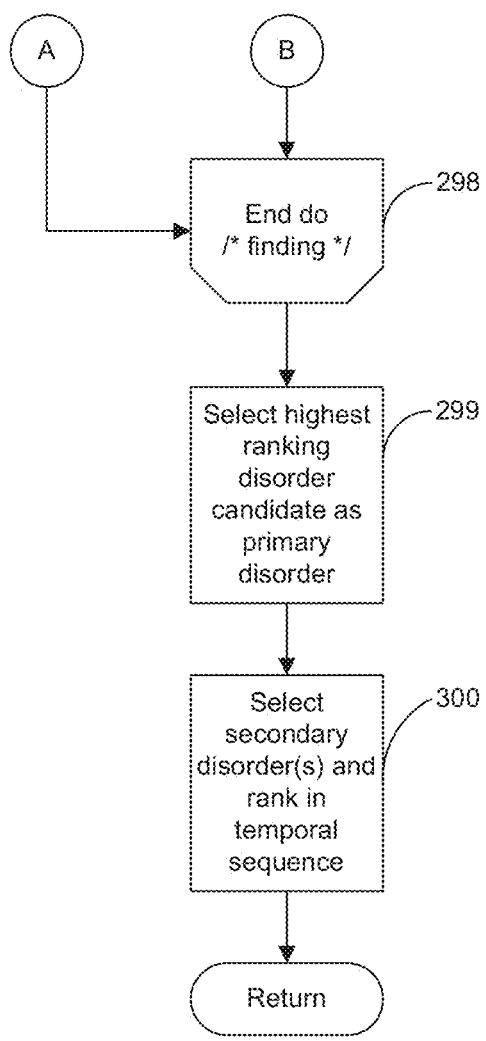

FIGS. 13A-13B are flow diagrams showing the routine for identifying disorder candidates 230 for use in the method of FIGS. 8A-8B. The purpose of this routine is to identify a primary or index disorder 212 and any secondary disorder(s). At this stage, all changes in physiological measures and quality of life and symptom measures have been identified and any matches between the changes and the pathophysiological indicators of each near-simultaneous disorder have been logged. The findings must now be ordered and ranked. First, the matched findings are sorted into temporal sequence (block 290), preferably from least recent to most recent. Next, each of the findings and each of the disorder candidates are iteratively processed in a pair of nested processing loops (blocks 291-298 and 292-297, respectively). Other forms of flow control are feasible, including recursive processing. Each finding is iteratively processed in the outer processing loop (blocks 291-298) beginning with the least recent finding. For each finding, each disorder candidate is iteratively processed during each inner processing loop (blocks 292-297) to determine the relative strength of any match. If the disorder candidate has a pathophysiological indicator which matches the current finding (block 293), the disorder candidate is ranked above any other disorder candidate not matching the current finding (block 294). This form of ranking ensures the disorder candidate with a pathophysiological indicator matching a least recent change in measure is considered ahead of other disorder candidates which may be secondary disorders. In addition, if the measure is prioritized (block 295), that is, the measure is a member of a group of related linked measures which have also changed or is an a priori measure, the ranking of the disorder candidate is increased (block 296). Iterative processing of disorders (blocks 292-297) continues until all disorder candidates have been considered. Similarly, iterative processing of findings (blocks 291-298) continues until all findings have been evaluated, whereupon the highest ranking disorder candidate is identified as the primary or index disorder 212 (shown in FIG. 5) (block 299). If other disorders rank close to the primary or index disorder and similarly reflect a strong match to the set of findings, any secondary disorder(s) are likewise identified and temporally ranked (block 300). The routine then returns.

While the invention has been particularly shown and described as referenced to the embodiments thereof, those skilled in the art will understand that the foregoing and other changes in form and detail may be made therein without departing from the spirit and scope of the invention.

What is claimed is:

1. A method for providing an index disorder for use in automated patient care, comprising:
   storing a set of device measures in a database;
   providing quantitative health care data indicators in the database, wherein the indicators were regularly recorded by a medical device for a patient under automated patient care;
   retrieving the device measures with a server system
   deriving measures from the device measures with the server system;
   performing statistical calculations for at least a portion of the indicators;
   quantifying a plurality of physiological changes based on one or more of the derived measures, the indicators, and the device measures;
   ordering the plurality of physiological changes in temporal sequence with a diagnostic module; and
   identifying the index disorder through the derived measure determination, the ordering of the one or more physiological changes, and the statistical calculation with the server system.

2. A method according to claim 1, further comprising:
   identifying, with a categorizing component, the index disorder from a plurality of index disorder candidates as having a pathophysiology substantially matching the change in physiology that occurred substantially least recently.

3. A method according to claim 1, wherein quantifying a plurality of physiological changes further comprises:
   quantifying a first physiological change in a first time window and quantifying the first physiological change within a different time window.

4. A method according to claim 1, further comprising:
   sorting, with an evaluation component, the plurality of physiological changes into a symptomatic event ordering set for at least one index disorder candidate; and
   evaluating, with the evaluation component, each physiological change in the symptomatic event ordering set for matched pathophysiology.

5. A method according to claim 1, further comprising:
   prioritizing, with a comparison component, the physiological changes using a predefined ordering, wherein physiological changes that occurred least recently are given higher priority than physiological changes that occurred most recently; and
   comparing, with the comparison component, the physiological changes to pathophysiological indicators for one or more index disorder candidates, wherein physiological changes having higher priorities are compared before the physiological changes having lower priorities.

6. A method according to claim 1, further comprising:

tracking, with a hysteresis component, temporal changes in physiology;

applying, with the hysteresis component, a stickiness threshold to the temporal changes; and determining whether interventive changes are appropriate based on applying the stickiness threshold to the temporal changes.

7. A method according to claim 1, further comprising:

testing, with a testing component, the physiological changes against one or more indicator thresholds to determine a patient status indicating at least one of a change and a status quo of the index disorder;

wherein the stored indicator threshold corresponds to a pathophysiology indicative of at least one of congestive heart failure, myocardial ischemia, respiratory insufficiency, and atrial fibrillation index disorders.

* * * * *